(12) United States Patent
Gustow et al.

(10) Patent No.: US 7,390,505 B2
(45) Date of Patent: *Jun. 24, 2008

(54) NANOPARTICULATE TOPIRAMATE FORMULATIONS

(75) Inventors: Evan Gustow, Villanova, PA (US); Tuula Ryde, Malvern, PA (US); Eugene R. Cooper, Berwyn, PA (US)

(73) Assignee: Elan Pharma International, Ltd., County Clare (IE)

( * ) Notice: Subject to any disclaimer, the term of this patent is extended or adjusted under 35 U.S.C. 154(b) by 512 days.

This patent is subject to a terminal disclaimer.

(21) Appl. No.: 10/766,960

(22) Filed: Jan. 30, 2004

(65) Prior Publication Data

US 2004/0258758 A1 Dec. 23, 2004

Related U.S. Application Data

(60) Provisional application No. 60/511,318, filed on Oct. 16, 2003, provisional application No. 60/477,789, filed on Jun. 12, 2003, provisional application No. 60/444,377, filed on Jan. 31, 2003.

(51) Int. Cl.
*A61K 9/14* (2006.01)
*A61K 31/335* (2006.01)
*A01N 43/02* (2006.01)

(52) U.S. Cl. ........................... 424/489; 514/449

(58) Field of Classification Search ............... 424/489; 514/449
See application file for complete search history.

(56) References Cited

U.S. PATENT DOCUMENTS

| | | | |
|---|---|---|---|
| 4,783,484 A | 11/1988 | Violante et al. |
| 4,826,689 A | 5/1989 | Violanto et al. |
| 4,997,454 A | 3/1991 | Violante et al. |
| 5,145,684 A | 9/1992 | Liversidge et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon |
| 5,336,507 A | 8/1994 | Na et al. |
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,399,363 A | 3/1995 | Liversidge et al. |

(Continued)

FOREIGN PATENT DOCUMENTS

| WO | WO 00/72973 A1 | 12/2000 |
|---|---|---|
| WO | WO 02/098565 A1 | 12/2002 |

OTHER PUBLICATIONS

Bray et al., "A 6-Month Radonmized, Placebo-Controlled, Dose-Ranging Trial of Topiramate for Weight Loss in Obesity", *Obesity Research*, 11:722-733 (2003).
Brookhaven National Laboratory (BNL), "Therapeutic Drug Blocks Nicotine's Effects on Brain Chemistry", (Nov. 8, 2001), http://www.bnl.gov/bnlweb/pubaf/pr/2001/bnlpr110801.htm.

(Continued)

*Primary Examiner*—Johann R. Richter
*Assistant Examiner*—Konata M. George
(74) *Attorney, Agent, or Firm*—Foley & Lardner LLP

(57) ABSTRACT

The present invention is directed to nanoparticulate compositions comprising topiramate. The topiramate particles of the composition have an effective average particle size of less than about 2 microns.

107 Claims, 2 Drawing Sheets

U.S. PATENT DOCUMENTS

| | | | |
|---|---|---|---|
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,622,938 A | 4/1997 | Wong |
| 5,628,981 A | 5/1997 | Liversidge et al. |
| 5,643,552 A | 7/1997 | Illig |
| 5,662,883 A | 9/1997 | Bagchi et al. |
| 5,665,331 A | 9/1997 | Bagchi et al. |
| 5,718,388 A | 2/1998 | Czekai et al. |
| 5,718,919 A | 2/1998 | Ruddy et al. |
| 5,741,522 A | 4/1998 | Violante et al. |
| 5,747,001 A | 5/1998 | Wiedmann et al. |
| 5,776,496 A | 7/1998 | Violante et al. |
| 5,834,025 A | 11/1998 | De Garavilla et al. |
| 5,862,999 A | 1/1999 | Czekai et al. |
| 6,045,829 A | 4/2000 | Liversidge et al. |
| 6,068,858 A | 5/2000 | Liversidge et al. |
| 6,153,225 A | 11/2000 | Lee et al. |
| 6,165,506 A | 12/2000 | Jain et al. |
| 6,207,197 B1 | 3/2001 | Ilum et al. |
| 6,221,400 B1 | 4/2001 | Liversidge et al. |
| 6,264,922 B1 | 7/2001 | Wood et al. |
| 6,267,989 B1 | 7/2001 | Liversidge et al. |
| 6,270,806 B1 | 8/2001 | Liversidge et al. |
| 6,316,029 B1 | 11/2001 | Jain et al. |
| 6,375,986 B1 | 4/2002 | Ryde et al. |
| 6,428,814 B1 | 8/2002 | Bosch |
| 6,431,478 B1 | 8/2002 | Reed et al. |
| 6,432,381 B2 | 8/2002 | Liversidge et al. |
| 6,582,285 B2 | 6/2003 | Czekai et al. |
| 6,592,903 B2 * | 7/2003 | Ryde et al. ............ 424/489 |
| 6,656,504 B1 | 12/2003 | Bosch et al. |
| 6,696,091 B2 * | 2/2004 | Thakur et al. ............ 424/490 |
| 2002/0012675 A1 | 1/2002 | Jain et al. |
| 2002/0110597 A1 | 8/2002 | Ryde et al. |
| 2004/0258757 A1 * | 12/2004 | Bosch et al. ............ 424/489 |
| 2005/0244503 A1 | 11/2005 | Rabinow et al. |

OTHER PUBLICATIONS

L. Henderson et al., "J & J will not pursue Topamax for Obesity", *BTech News*, (Feb. 8, 2002) (www.btechnews.com).

Johnson et al., "Oral topiramate for treatment of alcohol dependence: a randonmized controlled trial", *Lancet*, 361(9370): 1666-7 (May 17, 2003).

Lindahl et al., "Characterization of Fluids from the Stomach and Proximal Jejunum in Men and Women", *Pharmaceutical Research*, vol. 14, No. 4, pp. 497-502 (1997).

*The Physicians' Desk Reference*, 57th Ed., pp. 2501-2503 (2003).

Stein, "Epilepsy Drugs May Curb Obesity", *Wash. Post*, p. A03 (Oct. 7, 2003).

Stein, International Diabetes Federation (IDF): Topiramate Shows Potential for Weight Loss Obese Diabetics (Aug. 26, 2003), www.docguide.com/news/content.nsf/news/8525697700573E1885256D8E005999FC.

* cited by examiner

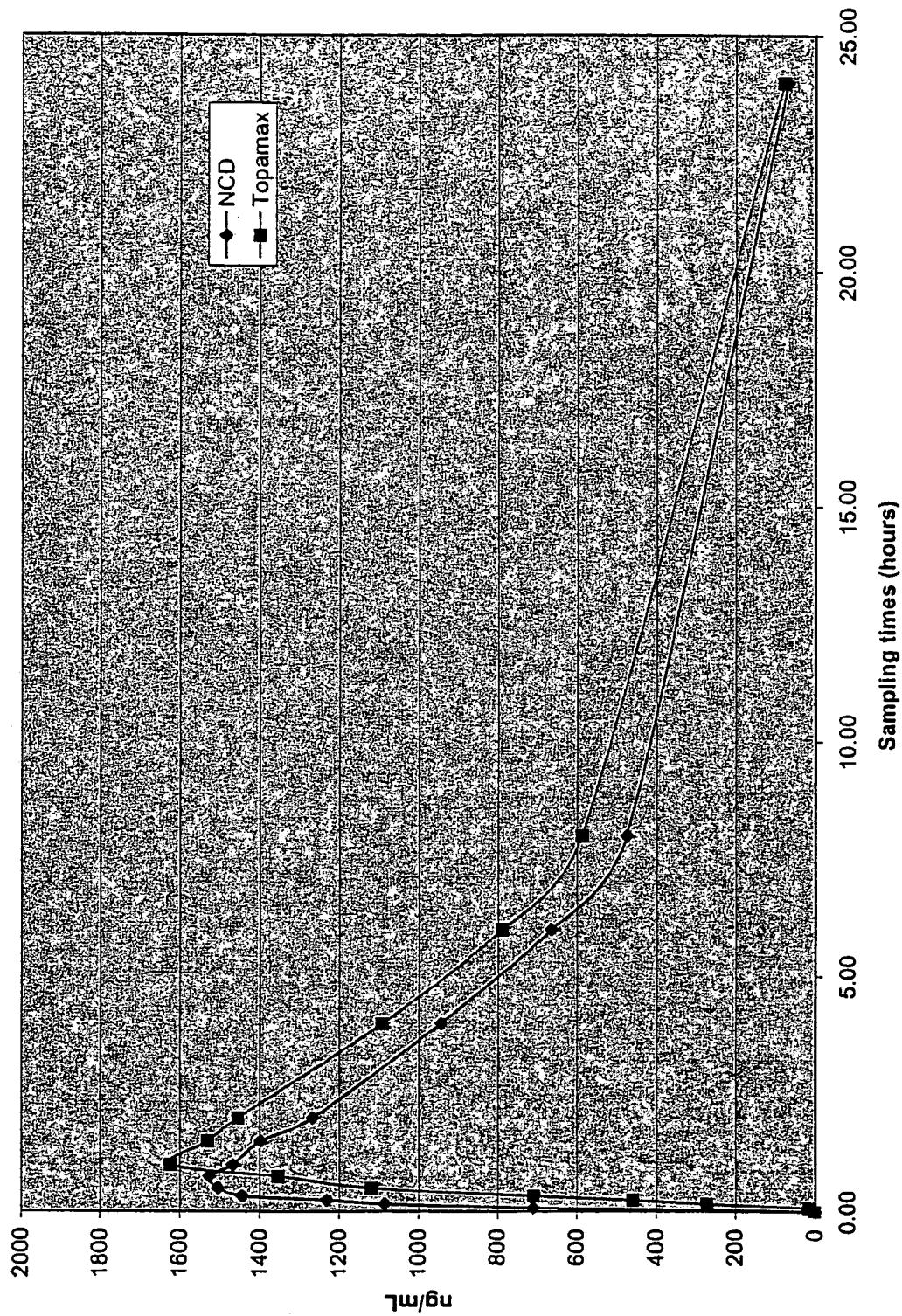
Figure 1: Nanoparticulate Topiramate Dispersion (NCD) vs TOPAMAX

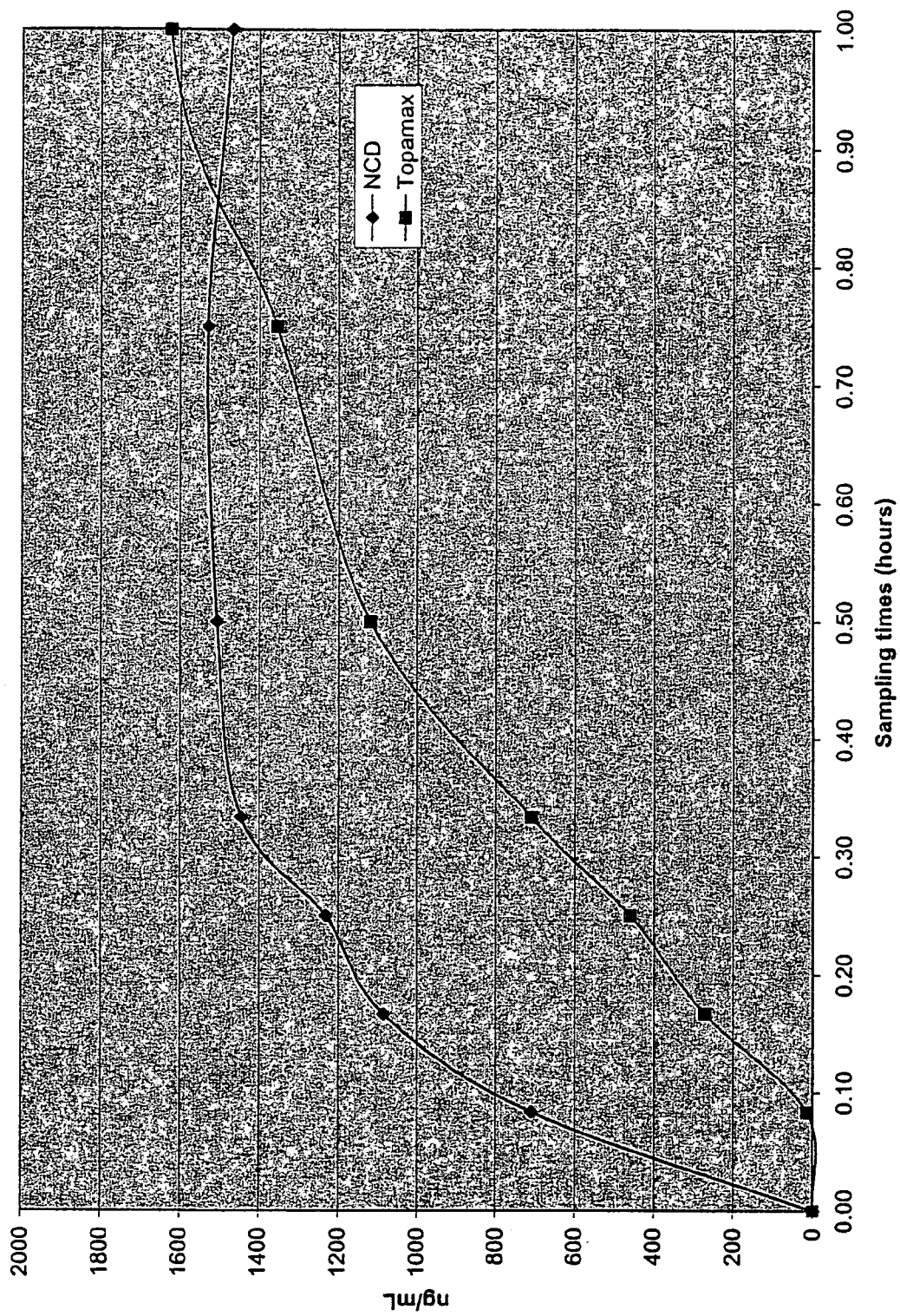
Figure 2: Nanoparticulate Topiramate Dispersion (NCD) vs TOPAMAX

NANOPARTICULATE TOPIRAMATE FORMULATIONS

CROSS-REFERENCE TO RELATED APPLICATIONS

The present invention claims benefit of U.S. Provisional Application No. 60/444,377, filed on Jan. 31, 2003; U.S. Provisional Application No. 60/477,789, filed on Jun. 12, 2003; and U.S. Provisional Application No. 60/511,318, filed on Oct. 16, 2003.

FIELD OF THE INVENTION

The present invention relates to a nanoparticulate composition comprising topiramate and at least one surface stabilizer that is preferably adsorbed to or associated with the surface of the drug. The nanoparticulate topiramate particles have an effective average particle size of less than about 2000 nm.

BACKGROUND OF THE INVENTION

A. Background Regarding Nanoparticulate Compositions

Nanoparticulate compositions, first described in U.S. Pat. No. 5,145,684 ("the '684 patent"), are particles consisting of a poorly soluble therapeutic or diagnostic agent having adsorbed onto or associated with the surface thereof a non-crosslinked surface stabilizer. The '684 patent does not describe nanoparticulate compositions of topiramate.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anhydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(–)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive nanoparticulate compositions having cationic surface stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract," U.S. Pat. No. 6,582,285 for "Apparatus for Sanitary Wet Milling," U.S. Pat. No. 6,592,903 for "Nanoparticulate Dispersions Comprising a Synergistic Combination of a Polymeric Surface Stabilizer and Dioctyl Sodium Sulfosuccinate," and U.S. Pat. No. 6,656,504 for "Nanoparticulate Compositions Comprising Amorphous Cyclosporine and Methods of Making and Using Such Compositions," all of which are specifically incorporated by reference.

In addition, U.S. Patent Application No. 20020012675 A1, published on Jan. 31, 2002, for "Controlled Release Nanoparticulate Compositions," and WO 02/098565 for "System and Method for Milling Materials," describe nanoparticulate active agent compositions, and are specifically incorporated by reference. None of these references describe nanoparticulate compositions of topiramate.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

B. Background Regarding Topiramate

Topiramate is a sulfamate-substituted monosaccharide designated chemically as 2,3:4,5-Di-O-isopropylidene-β-D-fructopyranose sulfamate, having the molecular formula $C_{12}H_{21}NO_8S$, a molecular weight of 339.36, and the following structural formula:

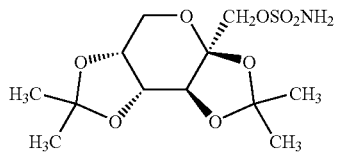

Topiramate has a solubility in water of 9.8 mg/mL. It is most soluble in alkaline solutions containing sodium hydroxide or sodium phosphate and having a pH of 9 to 10. Topiramate is freely soluble in acetone, chloroform, dimethylsulfoxide, and ethanol. See *Physicians' Desk Reference*, 57th Edition, pp. 2501 (2003). Topiramate is a white crystalline powder with a bitter taste.

Topiramate is an anticonvulsant intended for use as an antiepileptic drug. It is considered a broad spectrum antiepileptic drug (AED) because it works to prevent both partial onset and generalized seizures. Epilepsy is a chronic condition characterized by recurrent, unprovoked seizures, or electrical disturbances in the brain that can alter a patient's consciousness, movement, or behaviors. Seizures are characterized as either partial or generalized, depending on where they originate in the brain. Epilepsy affects an estimated 2.3 million Americans and each year approximately 181,000 people in the United States are newly diagnosed with the condition.

Topiramate is chemically unrelated to any other anticonvulsant or mood regulating medication. Topiramate has potentially five mechanisms of action. They include the blockage of sodium channels (similar to many of the traditional epileptics), enhancement of GABA-a receptors (an inhibitory neurotransmitter), inhibitory effect on glutamate receptors, inhibition of L-type high-voltage calcium ion channels, and a diamox type effect. The relatively importance of these mechanisms in the functioning of topiramate is not clearly known but it does not appear that any other single AED shares these five properties.

Specifically, topiramate enhances a chemical substance that inhibits electrical activity in the brain, while blocking other substances that increase activity. Thus, topiramate appears to help balance electrical activity in the brain to reduce the frequency of seizures. Electrophysiological and biochemical studies of the effects of topiramate on cultured neurons have revealed three properties that may contribute to topiramate's antiepileptic efficacy. First, action potentials elicited repetitively by a sustained depolarization of the neurons are blocked by topiramate in a time-dependent manner, suggestive of a state-dependent sodium channel blocking action. Second, topiramate increases the frequency at which γ-aminobutyrate (GABA) activates $GABA_A$ receptors, and enhances the ability of GABA to induce a flux of chloride ions into neurons, suggesting that topiramate potentiates the activity of this inhibitory neurotransmitter. Third, topiramate antagonizes the ability of kainae to activate the kainate/AMPA (α-amino-3-hydroxy-5-methylisoxazole-4-propionic acid, non-NMDA) subtype of excitatory amino acid (glutamate) receptor, but has no apparent effect on the activity of N-methyl-D-aspartate (NMDA) at the NMDA receptor subtype.

Patients newly diagnosed with epilepsy are routinely prescribed multiple medications to treat their seizures. The results of a recent study demonstrate that topiramate has a significant effect on controlling seizures in newly diagnosed epilepsy patients, even when used as a stand-alone therapy. See "New Study Shows TOPAMAX® Used Alone Helps Many Newly-Diagnosed Epilepsy Patients Achieve Seizure Control," (Dec. 11, 2002). Currently, topiramate is approved around the world as adjunctive (add-on) treatment for a variety of seizure types. In addition, more than 30 countries also have approved its use as stand-alone (monotherapy) treatment for epilepsy. In the United States, an application for this use was filed with the Food and Drug Administration in October 2002. If approved, topiramate will be the first AED indicated for initial monotherapy treatment for both partial and generalized tonic-clonic seizures in children and adults. Id.

Topiramate seems to be effective in some people with bipolar mood disorders that have not responded to lithium and/or other mood-stabilizers. Some people who have not been able to tolerate any antidepressant because of switches to mania or increased speed or intensity of cycling, or because of the development of mixed states, have been able to tolerate therapeutic doses of anti-depressants when taking topiramate. The weight loss that accompanies topiramate therapy in some instances is useful for those individuals who have gained weight while taking other mood stabilizing drugs. In some studies 20-50% of people taking topiramate lost weight.

Topiramate is also used for indications other than epilepsy. Among the most common uses of topiramate is the prevention of migraines. Less commonly than some of the other AEDs, topiramate is used for neuropathic pain relief. In some groups of patients, diabetics for example, the potential of weight loss is desirable and may therefore be a major reason for trying this medication for the treatment of diabetic neuropathic pain. Topiramate has also been shown in open label trials to be useful for treating essential type tremor. In addition, topiramate has been shown in multiple small trials to be effective in cluster headache. Finally, topiramate is also used by psychiatrists. A recent article in *Lancet* demonstrated a substantial benefit for using this medication to help alcoholics to quit drinking. See Johnson et al., "Oral topiramate for treatment of alcohol dependence: a randomized controlled trial," *Lancet*, 361(9370):1666-7 (May 17, 2003).

Topiramate is commercially available as TOPAMAX® (Ortho-McNeil Pharmaceutical, Raritan, N.J.). TOPAMAX® is available in tablet of various sizes as well as a sprinkle form which can be used in those who cannot swallow. It is typically dosed twice daily. TOPAMAX® (topiramate) is available as 25 mg, 100 mg, and 200 mg round tablets for oral administration. The tablets contain the following inactive ingredients: lactose monohydrate, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide (100 and 200 mg tablets), and polysorbate 80. *Physicians' Desk Reference*, 57$^{th}$ Edition, pp. 2501 (2003).

TOPAMAX® is indicated in the United States as adjunctive therapy for adults and children aged 2-16 with partial-onset seizures, primary generalized tonic-clonic seizures, and in patients 2 years of age and older with seizures associated with Lennox-Gastaut syndrome.

Peak plasma concentrations of TOPAMAX® occur at approximately 2 hours following a 400 mg oral dose. The relative bioavailability of TOPAMAX® from the tablet formulation is about 80% compared to a solution. The bioavailability of TOPAMAX® is not affected by food. *Physicians' Desk Reference* at 2502.

The pharmacokinetics of TOPAMAX® are linear with dose proportional increases in plasma concentration over the dose range studied (200 to 800 mg/day). The mean plasma elimination half-life is 21 hours after single or multiple doses. Steady state is reached in about 4 days in patients with normal renal function. Id.

TOPAMAX® is not extensively metabolized and is primarily eliminated unchanged in the urine (approximately 70% of an administered dose). Overall, oral plasma clearance is approximately 20 to 30 mL/min in humans following oral administration. Id.

The recommended total daily dose of TOPAMAX® as adjunctive therapy is 400 mg/day in two divided doses. In studies of adults with partial onset seizures, a daily dose of 200 mg/day has inconsistent effects and is less effective than 400 mg/day. It is recommended that therapy be initiated at 25-50 mg/day followed by titration to an effective dose in increments of 25-50 mg/week. Id.

In clinical trials of TOPAMAX® used as adjunctive therapy for partial-onset seizures, primary generalized tonic-clonic seizures, and seizures associated with Lennox-Gastaut syndrome, the most common side effects observed in children included excessive drowsiness, loss of appetite, fatigue, nervousness, difficulty with concentration/attention, weight loss, aggressive reaction and memory difficulties. In adults, the most common side effects were sleepiness, dizziness, poor coordination, speech difficulties, slowed thinking (psychomotor slowing), blurred or double vision, memory difficulties and changes in sensation. However, these effects were generally temporary. *Physicians' Desk Reference* at 2502-03.

TOPAMAX® lacks many of the more serious side effects seen with the older AEDs including a lack of known problems with bone marrow and an extremely small incidence of liver abnormalities apparently confined to patients with prior liver abnormalities. The drug does have a fairly common side effect of kidney stones (between 1-2%). It is also one of only two AEDs that have a statistically proven propensity to lose weight (Felbamate is the other). Other side effects include a change in taste, particularly with carbonated drinks, tingling in the extremities, and at times interference with mental function. The last side effect is highly dependent upon the rate of dose administration and is relatively uncommon among patients started at a low dose and advanced slowly. Dosing rates must be individualized based upon the patient and the other medications they are currently prescribed.

The following adverse events are related to topiramate in 5% or more of patients: ataxia, impaired concentration, confusion, dizziness, fatigue, paraesthesia, somnolence and abnormal thinking. Topiramate may also cause agitation and emotional lability (which may manifest as abnormal behavior) and depression. Less common adverse effects include amnesia, anorexia, aphasia, diplopia, nausea, nystagmus, speech disorder, alteration of the sense of taste, abnormal vision, and weight loss. Topiramate increases the risk of nephrolithiasis (formation of kidney stones).

There is a need in the art for topiramate formulations which can decrease frequency of dosing, improve clinical efficacy, and potentially reduce side effects. The present invention satisfies these needs.

SUMMARY OF THE INVENTION

The present invention relates to nanoparticulate compositions comprising topiramate. The compositions comprise topiramate and at least one surface stabilizer preferably adsorbed on or associated with the surface of the topiramate particles. The nanoparticulate topiramate particles have an effective average particle size of less than about 2 microns.

Another aspect of the invention is directed to pharmaceutical compositions comprising a nanoparticulate topiramate composition of the invention. The pharmaceutical compositions preferably comprise topiramate, at least one surface stabilizer, and at least one pharmaceutically acceptable carrier, as well as any desired excipients.

The present invention is also directed to topiramate compositions with improved pharmacokinetic profiles over traditional forms of topiramate. In particular, the nanoparticulate topiramate formulations of the invention may produce the same therapeutic effect with lower and/or fewer doses. Such lower doses are preferred as they may decrease or eliminate adverse effects of the drug. In addition, such lower doses decrease the cost of the dosage form and may increase patient compliance.

In yet another embodiment, the invention is directed to bioadhesive nanoparticulate topiramate formulations. Such compositions, when orally administered, adhere to the gut increasing the time for absorption, and thereby increasing the effectiveness of the dosage form.

Other advantages of the nanoparticulate topiramate compositions of the invention are described herein.

The invention further discloses a method of making a nanoparticulate topiramate composition. Such a method comprises contacting topiramate and at least one surface stabilizer for a time and under conditions sufficient to provide a nanoparticulate topiramate composition. The one or more surface stabilizers can be contacted with topiramate either before, preferably during, or after size reduction of the topiramate.

The present invention is also directed to methods of treatment using the nanoparticulate topiramate compositions of the invention for conditions such as, but not limited to, seizures, mood disorders, post traumatic stress syndrome (PTSD), Bipolar Disorder, mania (all forms, such as acute mania, severe treatment-refractory mania, bipolar mania, etc.), depression, personality disorders, bipolar mood instability, schizophrenia, psychosis, bipolar spectrum disorders, rapid-cycling bipolar disorders, etc. The nanoparticulate topiramate compositions of the invention are also useful for treating patients with mood disorders or bipolar mood disorders that have not been adequately controlled by other medications, such as lithium, lamotrigine, gabapentin, and/or other mood-stabilizers.

In other embodiments of the invention, the nanoparticulate topiramate compositions are useful in treating or preventing, for example, migraines, neuropathic pain relief, essential type tremor, cluster headache, and addictive behaviors, such as alcoholism, nicotine addiction, drug addiction, and food addiction.

Finally, the nanoparticulate topiramate compositions of the invention are useful for achieving weight loss, particularly when diet and exercise fail to result in a patient's ideal body weight.

Both the foregoing general description and the following brief description of the drawings and detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 1: Graphically shows the average concentration (ng/mL) of topiramate following oral administration to four male dogs of a nanoparticulate topiramate dispersion as compared to a conventional composition of topiramate, TOPAMAX®, over a 25 hour time period; and FIG. 2: Graphically shows the average concentration (ng/mL) of topiramate following oral administration to four male dogs of a nanoparticulate topiramate dispersion as compared to a conventional composition of topiramate, TOPAMAX®, over a 1 hour time period.

DETAILED DESCRIPTION OF THE INVENTION

The present invention is directed to nanoparticulate compositions comprising topiramate. The compositions comprise topiramate and at least one surface stabilizer that is preferably adsorbed on or associated with the surface of the drug. The nanoparticulate topiramate particles have an effective average particle size of less than about 2 microns.

As taught in the '684 patent, not every combination of surface stabilizer and active agent will result in a stable nanoparticulate composition. It was surprisingly discovered that stable nanoparticulate topiramate formulations can be made.

The current formulations of topiramate suffer from the following problems: (1) the poor solubility of the drug results in a relatively low bioavailability; (2) dosing must be repeated several times each day; and (3) a wide variety of side effects are associated with the current dosage forms of the drug.

The present invention overcomes problems encountered with the prior art topiramate formulations. Specifically, the nanoparticulate topiramate formulations of the invention may offer the following advantages: (1) faster onset of action; (2) a potential decrease in the frequency of dosing; (3) smaller doses of topiramate required to obtain the same pharmacological effect as compared to conventional microcrystalline forms of topiramate; (4) low viscosity liquid nanoparticulate topiramate dosage forms can be made; (5) for liquid nanoparticulate topiramate compositions having a low viscosity—better subject compliance due to the perception of a lighter formulation which is easier to consume and digest; (6) for liquid nanoparticulate topiramate compositions having a low viscosity—ease of dispensing because one can use a cup or a syringe; (7) increased bioavailability; (8) substantially similar pharmacokinetic profiles of the nanoparticulate topiramate compositions when administered in the fed versus the fasted state; (9) bioequivalency of the nanoparticulate topiramate compositions when administered in the fed versus the fasted state; (10) the nanoparticulate topiramate compositions may have improved pharmacokinetic profiles as compared to traditional forms of topiramate, such as improved $T_{max}$, $C_{max}$, and AUC profiles; (11) the topiramate composition can be formulated in a dried form which readily redisperses; (12) excellent redispersibility of the nanoparticulate topiramate particles present in the compositions of the invention following administration; (13) the nanoparticulate topiramate compositions preferably exhibit an increased rate of dissolution as compared to conventional microcrystalline forms of topiramate; (14) a bioadhesive topiramate formulation can coat the gut, or the desired site of application, and be retained for a period of time, thereby increasing the efficacy of the drug as well as eliminating or decreasing the frequency of dosing; (15) the nanoparticulate topiramate compositions can be used in conjunction with other active agents; (16) the nanoparticulate topiramate compositions can be sterile filtered; (17) the nanoparticulate topiramate compositions may exhibit improved performance characteristics for oral, intravenous, subcutaneous, or intramuscular injection, such as higher dose loading and smaller tablet or liquid dose volumes; (18) the nanoparticulate topiramate compositions are suitable for parenteral administration; and (19) the nanoparticulate topiramate compositions do not require organic solvents or pH extremes.

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" as used herein refers to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

As used herein with reference to stable drug particles, "stable" includes, but is not limited to, one or more of the following parameters: (1) that the topiramate particles do not appreciably flocculate or agglomerate due to interparticle attractive forces, or otherwise significantly increase in particle size over time; (2) that the physical structure of the topiramate particles is not altered over time, such as by conversion from an amorphous phase to crystalline phase; (3) that the topiramate particles are chemically stable; and/or (4) where the topiramate has not been subject to a heating step at or above the melting point of the topiramate in the preparation of the nanoparticles of the invention.

"Conventional active agents or drugs" refers to non-nanoparticulate compositions of active agents or solubilized active agents or drugs. Non-nanoparticulate active agents have an effective average particle size of greater than about 2 microns, meaning that at least 50% of the active agent particles have a size greater than about 2 microns. (Nanoparticulate active agents as defined herein have an effective average particle size of less than about 2 microns.)

"Therapeutically effective amount" as used herein with respect to a drug dosage, shall mean that dosage that provides the specific pharmacological response for which the drug is administered in a significant number of subjects in need of such treatment. It is emphasized that 'therapeutically effective amount,' administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

A. Preferred Characteristics of the Nanoparticulate Topiramate Compositions of the Invention 1. Fast Onset of Activity The use of conventional formulations of topiramate is not ideal due to delayed onset of action. In contrast, the nanoparticulate topiramate compositions of the invention exhibit faster therapeutic effects.

Topiramate is commercially available as TOPAMAX® (Ortho-McNeil Pharmaceutical, Raritan, N.J.). TOPAMAX® (topiramate) is available as 25 mg, 100 mg, and 200 mg round tablets for oral administration. See *Physicians' Desk Reference*, 57th Edition, pp. 2501 (2003). Peak plasma concentrations of TOPAMAX® occur at approximately 2 hours following a 400 mg oral dose. See *Physicians' Desk Reference* at 2502.

When the nanoparticulate topiramate compositions of the invention are formulated into an oral dosage form (e.g., the dosage form of TOPAMAX®), peak plasma concentration of the nanoparticulate topiramate can be obtained in less than about 2 hours ($T_{max}$). In other embodiments of the invention, peak plasma concentration of the nanoparticulate topiramate can be obtained in less than about 110 min., less than about 100 min., less than about 90 min., less than about 80 min. less than about 70 min., less than about 60 min., less than about 50 min., less than about 40 min., less than about 30 min., less than about 25 min., less than about 20 min., less than about 15 min., less than about 10 min., less than about 5 min., or less than about 3 min.

2. Frequency of Dosing and Dosage Quantity

The recommended total daily dose of TOPAMAX® as adjunctive therapy is 400 mg/day in two divided doses. In studies of adults with partial onset seizures, a daily dose of 200 mg/day has inconsistent effects and is less effective than 400 mg/day. See *Physicians' Desk Reference*, 57th Edition, pp. 2502 (2003).

Dosages of topiramate for treating conditions other than epilepsy tend to be less.

In contrast, the topiramate compositions of the invention may be administered less frequently and at lower doses in dosage forms such as liquid dispersions, powders, sprays, solid re-dispersable dosage forms, ointments, creams, etc. Exemplary types of formulations useful in the present invention include, but are not limited to, liquid dispersions, gels, aerosols (pulmonary and nasal), ointments, creams, solid dose forms, etc. of nanoparticulate topiramate. Lower dosages can be used because the small particle size of the topiramate particles ensure greater absorption, and in the case of bioadhesive nanoparticulate topiramate compositions, the topiramate is retained at the desired site of application for a longer period of time as compared to conventional topiramate dosage forms.

In one embodiment of the invention, the therapeutically effective amount of the nanoparticulate topiramate compositions is $\frac{1}{6}$, $\frac{1}{5}$, $\frac{1}{4}$, $\frac{1}{3}^{rd}$, or $\frac{1}{2}$ of the therapeutically effective amount of a conventional non-nanoparticulate topiramate composition.

3. Low Viscosity

A liquid dosage form of a conventional microcrystalline or non-nanoparticulate topiramate composition would be expected to be a relatively large volume, highly viscous substance which would not be well accepted by patient populations. Moreover, viscous solutions can be problematic in parenteral administration because these solutions require a slow syringe push and can stick to tubing. In addition, conventional formulations of poorly water-soluble active agents, such as topiramate, tend to be unsafe for intravenous administration techniques, which are used primarily in conjunction with highly water-soluble substances.

Liquid dosage forms of the nanoparticulate topiramate compositions of the invention provide significant advantages over a liquid dosage form of a conventional topiramate microcrystalline compound. The low viscosity and silky texture of liquid dosage forms of the nanoparticulate topiramate compositions of the invention result in advantages in both preparation and use. These advantages include, for example:

(1) better subject compliance due to the perception of a lighter formulation which is easier to consume and digest; (2) ease of dispensing because one can use a cup or a syringe; (3) potential for formulating a higher concentration of topiramate resulting in a smaller dosage volume and thus less volume for the subject to consume; and (4) easier overall formulation concerns.

Liquid topiramate dosage forms which are easier to consume are especially important when considering juvenile patients, terminally ill patients, and elderly patients. Viscous or gritty formulations, and those that require a relatively large dosage volume, are not well tolerated by these patient populations. Liquid oral dosage forms can be particularly preferably for patient populations who have difficulty consuming tablets, such as infants and the elderly.

The viscosities of liquid dosage forms of nanoparticulate topiramate according to the invention are preferably less than about 1/200, less than about 1/175, less than about 1/150, less than about 1/125, less than about 1/100, less than about 1/75, less than about 1/50, or less than about 1/25 of a liquid oral dosage form of a conventional, non-nanoparticulate topiramate composition, at about the same concentration per ml of topiramate.

Typically the viscosity of liquid nanoparticulate topiramate dosage forms of the invention, at a shear rate of 0.1 (1/s), is from about 2000 mPa s to about 1 mPa s, from about 1900 mPa·s to about 1 mPa·s, from about 1800 mPa·s to about 1 mPa·s, from about 1700 mPa·s to about 1 mPa·s, from about 1600 mPa·s to about 1 mPa·s, from about 1500 mPa·s to about 1 mPa·s, from about 1400 mPa·s to about 1 mPa·s, from about 1300 mPa·s to about 1 mPa·s, from about 1200 mPa·s to about 1 mPa·s, from about 1100 mPa·s to about 1 mPa·s, from about 1000 mPa·s to about 1 mPa·s, from about 900 mPa·s to about 1 mPa·s, from about 800 mPa·s to about 1 mPa·s, from about 700 mPa·s to about 1 mPa·s, from about 600 mPa·s to about 1 mPa·s, from about 500 mPa·s to about 1 mPa·s, from about 400 mPa·s to about 1 mPa·s, from about 300 mPa·s to about 1 mPa·s, from about 200 mPa·s to about 1 mPa·s, from about 175 mPa·s to about 1 mPa·s, from about 150 mPa·s to about 1 mPa·s, from about 125 mPa·s to about 1 mPa·s, from about 100 mPa·s to about 1 mPa·s, from about 75 mPa·s to about 1 mPa·s, from about 50 mPa·s to about 1 mPa·s, from about 25 mPa·s to about 1 mPa·s, from about 15 mPa·s to about 1 mPa·s, from about 10 mPa·s to about 1 mPa·s, or from about 5 mPa·s to about 1 mPa·s. Such a viscosity is much more attractive for subject consumption and may lead to better overall subject compliance.

Viscosity is concentration and temperature dependent. Typically, a higher concentration results in a higher viscosity, while a higher temperature results in a lower viscosity. Viscosity as defined above refers to measurements taken at about 20° C. (The viscosity of water at 20° C. is 1 mPa s.) The invention encompasses equivalent viscosities measured at different temperatures.

Another important aspect of the invention is that the nanoparticulate topiramate compositions of the invention are not turbid. "Turbid," as used herein refers to the property of particulate matter that can be seen with the naked eye or that which can be felt as "gritty." The nanoparticulate topiramate compositions of the invention can be poured out of or extracted from a container as easily as water, whereas a liquid dosage form of a non-nanoparticulate or solubilized topiramate is expected to exhibit notably more "sluggish" characteristics.

The liquid formulations of this invention can be formulated for dosages in any volume but preferably equivalent or smaller volumes than a liquid dosage form of a conventional non-nanoparticulate topiramate composition.

4. Increased Bioavailability

The nanoparticulate topiramate compositions of the invention may preferably exhibit increased bioavailability and require smaller doses as compared to prior conventional topiramate compositions administered at the same dose.

Any drug, including topiramate, can have adverse side effects. Thus, lower doses of topiramate which can achieve the same or better therapeutic effects as those observed with larger doses of conventional topiramate compositions are desired. Such lower doses may be realized with the nanoparticulate topiramate compositions of the invention because the nanoparticulate topiramate compositions may exhibit greater bioavailability as compared to conventional non-nanoparticulate topiramate formulations, which means that smaller dose of topiramate are likely required to obtain the desired therapeutic effect.

The relative bioavailability of TOPAMAX® from the tablet formulation is about 80% compared to a solution. See *Physicians' Desk Reference* at 2502.

When the nanoparticulate topiramate compositions of the invention are formulated into an oral dosage form (e.g., the dosage form of TOPAMAX®), the relative bioavailability of the nanoparticulate topiramate composition compared to a solution is preferably greater than about 80%. In other embodiments of the invention, the relative bioavailability of the nanoparticulate topiramate composition as compared to a solution can preferably be greater than about 85%, greater than about 90%, or greater than about 95%.

5. The Pharmacokinetic Profiles of the Nanoparticulate Topiramate Compositions of the Invention are Preferably not Substantially Affected by the Fed or Fasted State of the Subject Ingesting the Compositions The invention encompasses nanoparticulate topiramate compositions wherein preferably the pharmacokinetic profile of the topiramate is not substantially affected by the fed or fasted state of a subject ingesting the composition. This means that there is no substantial difference in the quantity of topiramate absorbed or the rate of topiramate absorption when the nanoparticulate topiramate compositions are administered in the fed versus the fasted state. Thus, the nanoparticulate topiramate compositions of the invention substantially eliminate the effect of food on the pharmacokinetics of topiramate.

The difference in absorption of the nanoparticulate topiramate composition of the invention, when administered in the fed versus the fasted state, is preferably less than about 100%, less than about 90%, less than about 80%, less than about 70%, less than about 60%, less than about 50%, less than about 40%, less than about 35%, less than about 30%, less than about 25%, less than about 20%, less than about 15%, less than about 10%, less than about 5%, or less than about 3%. This is an especially important feature in treating patients with difficulty in maintaining a fed state.

In addition, preferably the difference in the rate of absorption (i.e., $T_{max}$) of the nanoparticulate topiramate compositions of the invention, when administered in the fed versus the fasted state, is less than about 100%, less than about 90%, less than about 80%, less than about 70%, less than about 60%, less than about 50%, less than about 40%, less than about 30%, less than about 20%, less than about 15%, less than about 10%, less than about 5%, less than about 3%, or essentially no difference.

Benefits of a dosage form which substantially eliminates the effect of food include an increase in subject convenience, thereby increasing subject compliance, as the subject does not need to ensure that they are taking a dose either with or without food.

6. Redispersibility Profiles of the Nanoparticulate Topiramate Compositions of the Invention An additional feature of the nanoparticulate topiramate compositions of the invention is that the compositions redisperse such that the effective average particle size of the redispersed topiramate particles is less than about 2 microns. This is significant, as if upon administration the nanoparticulate topiramate particles present in the compositions of the invention did not redisperse to a substantially nanoparticulate particle size, then the dosage form may lose the benefits afforded by formulating topiramate into a nanoparticulate particle size.

This is because nanoparticulate topiramate compositions benefit from the small particle size of topiramate; if the nanoparticulate topiramate particles do not redisperse into the small particle sizes upon administration, then "clumps" or agglomerated topiramate particles are formed. With the formation of such agglomerated particles, the bioavailability of the dosage form may fall.

Moreover, the nanoparticulate topiramate compositions of the invention exhibit dramatic redispersion of the nanoparticulate topiramate particles upon administration to a mammal, such as a human or animal, as demonstrated by reconstitution in a biorelevant aqueous media. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 M, and NaCl solutions, ranging in concentration from about 0.001 to about 0.1 M, and mixtures thereof. For example, electrolyte solutions can be, but are not limited to, about 0.1 M HCl or less, about 0.01 M HCl or less, about 0.001 M HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 M HCl, 0.01 M HCl, and 0.1 M HCl correspond to pH 3, pH 2, and pH 1, respectively. Thus, a 0.01 M HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+ sodium, potassium and calcium salts of chloride.

In other embodiments of the invention, the redispersed topiramate particles of the invention (redispersed in an aqueous, biorelevant, or any other suitable media) have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2000 nm" it is meant that at least 50% of the topiramate particles have a particle size of less than the effective average, by weight, i.e., less than about 2000 nm, 1900 nm, 1800 nm, etc., when measured by the above-noted techniques. Preferably, at least about 70%, about 90%, about 95%, or about 99% of the topiramate particles have a particle size of less than the effective average, i.e., less than about 2000 nm, 1900 nm, 1800 nm, 1700 nm, etc.

Redispersibility can be tested using any suitable means known in the art. See e.g., the example sections of U.S. Pat. No. 6,375,986 for "Solid Dose Nanoparticulate Compositions Comprising a Synergistic Combination of a Polymeric Surface Stabilizer and Dioctyl Sodium Sulfosuccinate."

7. Bioadhesive Nanoparticulate Topiramate Compositions

Bioadhesive nanoparticulate topiramate compositions of the invention comprise at least one cationic surface stabilizer, which are described in more detail below. Bioadhesive formulations of topiramate exhibit exceptional bioadhesion to biological surfaces, such as mucous.

In the case of bioadhesive nanoparticulate topiramate compositions, the term "bioadhesion" is used to describe the adhesion between the nanoparticulate topiramate compositions and a biological substrate (i.e. gastrointestinal mucin, lung tissue, nasal mucosa, etc.). See e.g., U.S. Pat. No. 6,428, 814 for "Bioadhesive Nanoparticulate Compositions Having Cationic Surface Stabilizers," which is specifically incorporated by reference.

The bioadhesive topiramate compositions of the invention are useful in any situation in which it is desirable to apply the compositions to a biological surface. The bioadhesive topiramate compositions preferably coat the targeted surface in a continuous and uniform film which is invisible to the naked human eye.

A bioadhesive nanoparticulate topiramate composition slows the transit of the composition, and some topiramate particles would also most likely adhere to tissue other than the mucous cells and therefore give a prolonged exposure to topiramate, thereby increasing absorption and the bioavailability of the administered dosage.

8. Pharmacokinetic Profiles of the Nanoparticulate Topiramate Compositions of the Invention The present invention also provides compositions of nanoparticulate topiramate having a desirable pharmacokinetic profile when administered to mammalian subject. The nanoparticulate topiramate compositions of the invention preferably have a more preferred pharmacokinetic profile as compared to conventional currently marketed forms of topiramate, e.g., TOPAMAX®.

The desirable pharmacokinetic profile, as used herein, is the pharmacokinetic profile measured after the initial dose of topiramate. The compositions can be formulated in any way as described below.

An improved or more preferred pharmacokinetic profile according to the invention can have several different types of attributes. For example, the improved pK profile of the nanoparticulate topiramate compositions of the invention may produce the same pK profile as a conventional topiramate formulation (i.e., TOPAMAX®), but at a lower dose. Such an improved pK profile may also correspond to a topiramate composition which requires less frequent dosing as compared to a conventional topiramate formulation, such as once a day dosing. An improved pK profile may show faster onset of activity and/or greater quantity of drug absorbed (i.e., greater bioavailability). The improved pK profile of the nanoparticulate topiramate compositions of the invention may permit more effective or faster titration of the patient to therapeutic doses, etc. Combinations of these examples of improved pK profiles may also be exhibited by the nanoparticulate topiramate compositions of the invention.

An improved or more preferred pharmacokinetic profile according to the invention may also exhibit improved $T_{max}$, $C_{max}$, and/or AUC profiles.

In one embodiment of the invention, preferably, the $T_{max}$ of an administered dose of a nanoparticulate topiramate composition is less than that of a conventional non-nanoparticulate topiramate composition, administered at the same dosage. In another embodiment of the invention, preferably the $C_{max}$ of a nanoparticulate topiramate composition is greater than the $C_{max}$ of a conventional non-nanoparticulate topiramate composition, administered at the same dosage. Finally, in yet another embodiment of the invnetion, preferably the AUC of a nanoparticulate topiramate composition is greater than the AUC of a conventional non-nanoparticulate topiramate composition, administered at the same dosage.

A preferred nanoparticulate topiramate composition of the invention may exhibit, in comparative pharmacokinetic testing with a conventional non-nanoparticulate formulation of topiramate, such as TOPAMAX®, a $T_{max}$ which is less than about 100%, less than about 90%, less than about 80%, less than about 70%, less than about 60%, less than about 50%, less than about 40%, less than about 30%, less than about 25%, less than about 20%, less than about 15%, or less than about 10% of the $T_{max}$ exhibited by the conventional non-nanoparticulate formulation of topiramate.

A preferred nanoparticulate topiramate composition of the invention may exhibit, in comparative pharmacokinetic testing with a conventional non-nanoparticulate formulation of topiramate, such as TOPAMAX®, a $C_{max}$ which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the $C_{max}$ exhibited by the conventional non-nanoparticulate formulation of topiramate.

A preferred nanoparticulate topiramate composition of the invention may exhibit, in comparative pharmacokinetic testing with a conventional non-nanoparticulate formulation of topiramate, such as TOPAMAX®, an AUC which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the AUC exhibited by the conventional non-nanoparticulate formulation of topiramate.

Any formulation giving the desired pharmacokinetic profile is suitable for administration according to the present methods. Exemplary types of formulations giving such profiles are liquid dispersions and solid dose forms of nanoparticulate topiramate. If the liquid dispersion media is one in which the nanoparticulate topiramate has very low solubility, the nanoparticulate topiramate particles are present as suspended particles. The smaller the topiramate particles, the higher the probability that the formulation will exhibit the desired pharmacokinetic profile.

9. Combination Pharmacokinetic Profile Compositions

In yet another embodiment of the invention, a first nanoparticulate topiramate composition providing a desired pharmacokinetic profile is co-administered, sequentially administered, or combined with at least one other topiramate composition that generates a desired different pharmacokinetic profile. More than two topiramate compositions can be co-administered, sequentially administered, or combined. While the first topiramate composition has a nanoparticulate particle size, the additional one or more topiramate compositions can be nanoparticulate, solubilized, or have a conventional microparticulate particle size.

For example, a first topiramate composition can have a nanoparticulate particle size, conferring a short $T_{max}$ and typically a higher $C_{max}$. This first topiramate composition can be combined, co-administered, or sequentially administered with a second composition comprising: (1) topiramate having a larger (but still nanoparticulate as defined herein) particle size, and therefore exhibiting slower absorption, a longer $T_{max}$, and typically a lower $C_{max}$; or (2) a microparticulate or solubilized topiramate composition, exhibiting a longer $T_{max}$, and typically a lower $C_{max}$.

The second, third, fourth, etc., topiramate compositions can differ from the first, and from each other, for example: (1) in the effective average particle sizes of topiramate; or (2) in the dosage of topiramate. Such a combination composition can reduce the dose frequency required.

If the second topiramate composition has a nanoparticulate particle size, then preferably the topiramate particles of the second composition have at least one surface stabilizer associated with the surface of the drug particles. The one or more surface stabilizers can be the same as or different from the surface stabilizer(s) present in the first topiramate composition.

Preferably where co-administration of a "fast-acting" formulation and a "longer-lasting" formulation is desired, the two formulations are combined within a single composition, for example a dual-release composition.

10. Combination Active Agent Compositions

The invention encompasses the nanoparticulate topiramate compositions of the invention formulated or co-administered with one or more non-topiramate active agents, which are either conventional (solubilized or microparticulate) or nanoparticulate. Methods of using such combination compositions are also encompassed by the invention. The non-topiramate active agents can be present in a crystalline phase, an amorphous phase, a semi-crystalline phase, a semi-amorphous phase, or a mixture thereof.

The compound to be administered in combination with a nanoparticulate topiramate composition of the invention can be formulated separately from the nanoparticulate topiramate composition or co-formulated with the nanoparticulate topiramate composition. Where a nanoparticulate topiramate composition is co-formulated with a second active agent, the second active agent can be formulated in any suitable manner, such as immediate-release, rapid-onset, sustained-release, or dual-release form.

If the non-topiramate active agent has a nanoparticulate particle size i.e., a particle size of less than about 2 microns, then preferably it will have one or more surface stabilizers associated with the surface of the active agent. In addition, if the active agent has a nanoparticulate particle size, then it is preferably poorly soluble and dispersible in at least one liquid dispersion media. By "poorly soluble" it is meant that the active agent has a solubility in a liquid dispersion media of less than about 30 mg/mL, less than about 20 mg/mL, less than about 10 mg/mL, or less than about 1 mg/mL. Useful liquid dispersion medias include, but are not limited to, water, aqueous salt solutions, safflower oil, and solvents such as ethanol, t-butanol, hexane, and glycol.

Such non-topiramate active agents can be, for example, a therapeutic agent. A therapeutic agent can be a pharmaceutical agent, including biologics. The active agent can be selected from a variety of known classes of drugs, including, for example, amino acids, proteins, peptides, nucleotides, anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of active agents and a listing of species within each class can be found in Martindale's *The Extra Pharmacopoeia,* $31^{st}$ Edition (The Pharmaceutical Press, London, 1996), specifically incorporated by reference. The active agents are commercially available and/or can be prepared by techniques known in the art.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. Dietary supplements and nutraceuticals are also disclosed in *Physicians' Desk Reference for Nutritional Supplements,* 1st Ed. (2001) and *The Physicians' Desk Reference for Herbal Medicines,* 1st Ed. (2001), both of which are also incorporated by reference. A nutraceutical or dietary supplement, also known as a phytochemical or functional food, is generally any one of a class of dietary supplements, vitamins, minerals, herbs, or healing foods that have medical or pharmaceutical effects on the body.

Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., arginine, iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bioengineered foods genetically engineered to have a desired property, also known as "pharmafoods."

11. Sterile Filtered Nanoparticulate Topiramate Compositions

The nanoparticulate topiramate compositions of the invention can be sterile filtered. This obviates the need for heat sterilization, which can harm or degrade topiramate, as well as result in crystal growth and particle aggregation.

Sterile filtration can be difficult because of the required small particle size of the composition. Filtration is an effective method for sterilizing homogeneous solutions when the membrane filter pore size is less than or equal to about 0.2 microns (200 nm) because a 0.2 micron filter is sufficient to remove essentially all bacteria. Sterile filtration is normally not used to sterilize conventional suspensions of micron-sized topiramate because the topiramate particles are too large to pass through the membrane pores.

A sterile nanoparticulate topiramate dosage form is particularly useful in treating immunocompromised patients, infants or juvenile patients, and the elderly, as these patient groups are the most susceptible to infection caused by a non-sterile liquid dosage form.

Because the nanoparticulate topiramate compositions of the invention can be sterile filtered, and because the compositions can have a very small topiramate effective average particle size, the compositions are suitable for parenteral administration.

12. Miscellaneous Benefits of the Nanoparticulate Topiramate Compositions of the Invention The nanoparticulate topiramate compositions preferably exhibit an increased rate of dissolution as compared to conventional microcrystalline or non-nanoparticulate forms of topiramate. In addition, the nanoparticulate topiramate compositions preferably exhibit improved performance characteristics for oral, intravenous, subcutaneous, or intramuscular injection, such as higher dose loading and smaller tablet or liquid dose volumes. Moreover, the nanoparticulate topiramate compositions of the invention do not require organic solvents or pH extremes.

B. Topiramate Compositions

The invention provides compositions comprising nanoparticulate topiramate particles and at least one surface stabilizer. The surface stabilizers are preferably associated with the surface of the topiramate particles. Surface stabilizers useful herein do not chemically react with the topiramate particles or itself. Preferably, individual molecules of the surface stabilizer are essentially free of intermolecular cross-linkages. The compositions can comprise two or more surface stabilizers.

The present invention also includes nanoparticulate topiramate compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration (in solid, liquid, or aerosol (i.e., pulmonary) form), vaginal, nasal, rectal, ocular, local (powders, creams, ointments or drops), buccal, intracisternal, intraperitoneal, topical administration, and the like.

1. Topiramate Particles

As used in this invention, "topiramate" means the sulfamate-substituted monosaccharide designated chemically as 2,3:4,5-Di-O-isopropylidene-β-D-fructopyranose sulfamate, having the molecular formula $C_{12}H_{21}$, $NO_8S$, a molecular weight of 339.36, and the following structural formula:

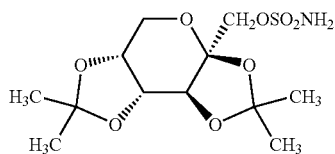

Derivatives of topiramate are also encompassed by the term "topiramate."

Topiramate has a solubility in water of 9.8 mg/mL. It is most soluble in alkaline solutions containing sodium hydroxide or sodium phosphate and having a pH of 9 to 10. Topiramate is freely soluble in acetone, chloroform, dimethylsulfoxide, and ethanol. See *Physicians' Desk Reference*, 57$^{th}$ Edition, pp. 2501 (2003). Topiramate is a white crystalline powder with a bitter taste.

The topiramate can be in a crystalline phase, an amorphous phase, a semi-crystalline phase, a semi-amorphous phase, or a mixtures thereof.

Topiramate is an anticonvulsant intended for use as an antiepileptic drug. The drug is useful in treating conditions such as, but not limited to, seizures, mood disorders, post traumatic stress syndrome (PTSD), Bipolar Disorder, mania (all forms, such as acute mania, severe treatment-refractory mania, bipolar mania, etc.), depression, personality disorders, bipolar mood instability, schizophrenia, psychosis, bipolar spectrum disorders, rapid-cycling bipolar disorders, etc. The nanoparticulate topiramate compositions of the invention are also useful for treating patients with mood disorders that have not been adequately controlled by other medications, such as lamotrigine and gabapentin, and for treating patients with bipolar mood disorders that have not responded to lithium and/or other mood-stabilizers.

2. Surface Stabilizers

The choice of a surface stabilizer for topiramate is non-trivial and required extensive experimentation to realize a desirable formulation. Accordingly, the present invention is directed to the surprising discovery that topiramate nanoparticulate compositions can be made.

Combinations of more than one surface stabilizer can be used in the invention. Useful surface stabilizers which can be employed in the invention include, but are not limited to, known organic and inorganic pharmaceutical excipients. Such excipients include various polymers, low molecular weight oligomers, natural products, and surfactants. Surface stabilizers include nonionic, cationic, zwitterionic, and ionic surfactants.

Representative examples of other useful surface stabilizers include hydroxypropyl methylcellulose, hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-lOG® or Surfactant 10-G®(Olin Chemicals, Stamford, Conn.); Crodestas SL-40(Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-p-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-derivatized phospholipid, PEG-derivatized cholesterol, PEG-derivatized cholesterol derivative, PEG-derivatized vitamin A, PEG-derivatized vitamin E, lysozyme, random copolymers of vinyl pyrrolidone and vinyl acetate, and the like.

Depending upon the desired method of administration, bioadhesive formulations of nanoparticulate topiramate can be prepared by selecting one or more cationic surface stabilizers that impart bioadhesive properties to the resultant composition. Useful cationic surface stabilizers are described below.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt) (also known as DPPE-PEG (2000)-Amine Na) (Avanti Polar Lipids, Alabaster, A1), Poly (2-methacryloxyethyl trimethylammonium bromide) (Polysciences, Inc., Warrington, Pa.) (also known as S1001), poloxamines such as Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.), lysozyme, long-chain polymers such as alginic acid, carrageenan (FMC Corp.), and POLYOX (Dow, Midland, Mich.).

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12}$-14) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric cationic surface stabilizers are any nonpolymeric compound, such as benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1R_4$ is $C_6H_5CH_2$, and one of $R_1R_4$ is an alkyl chain of seven carbon atoms or less;
(vi) two of $R_1$-$R_4$ are $CH_3$, one of $R_1R_4$ is $C_6H_5CH_2$, and one of $R_1R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-4 is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The surface stabilizers are commercially available and/or can be prepared by techniques known in the art.

3. Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

4. Nanoparticulate Topiramate Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

The compositions of the invention comprise topiramate nanoparticles which have an effective average particle size of less than about 2000 nm (i.e., 2 microns), less than about 1900 nm, less than less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, or less than about 50 nm, when measured by the above-noted techniques.

If the nanoparticulate topiramate composition additionally comprises one or more non-topiramate nanoparticulate active agents, then such active agents have an effective average particle size of less than about 2000 nm (i.e., 2 microns). In other embodiments of the invention, the nanoparticulate non-topiramate active agents can have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by the above-noted techniques.

By "an effective average particle size of less than about 2000 nm" it is meant that at least 50% of the nanoparticulate topiramate particles or nanoparticulate non-topiramate active agent particles have a weight average particle size of less than about 2000 nm, when measured by the above-noted techniques. In other embodiments of the invention, at least about 70%, at least about 90%, at least about 95%, or at least about 99% of the nanoparticulate topiramate particles or nanoparticulate non-topiramate active agent particles have a particle size of less than the effective average, by weight, i.e., less than about 2000 nm, less than about 1900 nm, less than less than about 1800 nm, less than about 1700 nm, etc.

If the nanoparticulate topiramate composition is combined with a conventional or microparticulate topiramate composition or non-topiramate active agent composition, then such a composition is either solubilized or has an effective average particle size of greater than about 2 microns. By "an effective average particle size of greater than about 2 microns" it is meant that at least 50% of the conventional topiramate or conventional non-topiramate active agent particles have a particle size of greater than about 2 microns, by weight, when measured by the above-noted techniques. In other embodiments of the invention, at least about 70%, about 90%, about 95%, or about 99%, by weight, of the conventional topiramate or conventional non-topiramate active agent particles have a particle size greater than about 2 microns.

In the present invention, the value for D50 of a nanoparticulate topiramate composition is the particle size below which 50% of the topiramate particles fall, by weight. Similarly, D90 is the particle size below which 90% of the topiramate particles fall, by weight.

5. Concentration of Nanoparticulate Topiramate and Surface Stabilizers

The relative amounts of topiramate and one or more surface stabilizers can vary widely. The optimal amount of the individual components can depend, for example, upon the hydrophilic lipophilic balance (HLB), melting point, and the surface tension of water solutions of the stabilizer, etc.

The concentration of topiramate can vary from about 99.5% to about 0.001%, from about 95% to about 0.1%, or from about 90% to about 0.5%, by weight, based on the total combined dry weight of the topiramate and at least one surface stabilizer, not including other excipients.

The concentration of the at least one surface stabilizer can vary from about 0.5% to about 99.999%, from about 5.0% to about 99.9%, or from about 10% to about 99.5%, by weight, based on the total combined dry weight of the topiramate and at least one surface stabilizer, not including other excipients.

C. Methods of Making Nanoparticulate Topiramate Formulations

The nanoparticulate topiramate compositions can be made using, for example, milling, homogenization, or precipitation techniques. Exemplary methods of making nanoparticulate compositions are described in the '684 patent. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

Following milling, homogenization, precipitation, etc., the resultant nanoparticulate topiramate compositions can be utilized in solid or liquid dosage formulations, such as controlled release formulations, solid dose fast melt formulations, aerosol formulations, nasal formulations, lyophilized formulations, tablets, capsules, solid lozenge, powders, creams, ointments, etc.

1. Milling to Obtain Nanoparticulate Topiramate Dispersions

Milling topiramate to obtain a nanoparticulate dispersion comprises dispersing topiramate particles in a liquid dispersion media in which topiramate is poorly soluble, followed by applying mechanical means in the presence of grinding media to reduce the particle size of topiramate to the desired effective average particle size. The dispersion media can be, for example, water, safflower oil, ethanol, t-butanol, glycerin, polyethylene glycol (PEG), hexane, or glycol.

The topiramate particles can be reduced in size in the presence of at least one surface stabilizer. Alternatively, the topiramate particles can be contacted with one or more surface stabilizers after attrition. Other compounds, such as a diluent, can be added to the topiramate/surface stabilizer composition during the size reduction process. Dispersions can be manufactured continuously or in a batch mode.

2. Precipitation to Obtain Nanoparticulate Topiramate Compositions

Another method of forming the desired nanoparticulate topiramate composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving topiramate in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by conventional means.

3. Homogenization to Obtain Topiramate Nanoparticulate Compositions

Exemplary homogenization methods of preparing active agent nanoparticulate compositions are described in U.S. Pat. No. 5,510,118, for "Process of Preparing Therapeutic Compositions Containing Nanoparticles."

Such a method comprises dispersing topiramate particles in a liquid dispersion media in which topiramate is poorly soluble, followed by subjecting the dispersion to homogenization to reduce the particle size of the topiramate to the desired effective average particle size. The dispersion media can be, for example, water, safflower oil, ethanol, t-butanol, glycerin, polyethylene glycol (PEG), hexane, or glycol.

The topiramate particles can be reduced in size in the presence of at least one surface stabilizer. Alternatively, the topiramate particles can be contacted with one or more surface stabilizers either before or after attrition. Other compounds, such as a diluent, can be added to the topiramate/surface stabilizer composition either before, during, or after the size reduction process. Dispersions can be manufactured continuously or in a batch mode.

D. Methods of Using Nanoparticulate Topiramate Formulations

The method of the invention comprises administering to a subject an effective amount of a composition comprising nanoparticulate topiramate. The topiramate compositions of the present invention can be administered to a subject via any conventional means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, powder aerosols, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable aerosols, emulsions, solutions, suspensions, syrups, and elixirs. In addition to the active agent, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

One of ordinary skill will appreciate that effective amounts of topiramate can be determined empirically and can be employed in pure form or, where such forms exist, in pharmaceutically acceptable salt, ester, or prodrug form. Actual dosage levels of topiramate in the nanoparticulate compositions of the invention may be varied to obtain an amount of topiramate that is effective to obtain a desired therapeutic response for a particular composition and method of administration. The selected dosage level therefore depends upon the desired therapeutic effect, the route of administration, the potency of the administered topiramate, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

1. Uses in Treating Epilepsy and Related Disorders

Depending on the mode of administration, the nanoparticulate topiramate compositions of the invention are useful in treating, for example, seizures, mood disorders, post traumatic stress syndrome (PTSD), Bipolar Disorder, mania (all forms, such as acute mania, severe treatment-refractory mania, bipolar mania, etc.), depression, personality disorders, bipolar mood instability, schizophrenia, psychosis, bipolar spectrum disorders, rapid-cycling bipolar disorders, etc. The nanoparticulate topiramate compositions of the invention are also useful for treating patients with mood disorders that have not been adequately controlled by other medications, such as lamotrigine and gabapentin, and for treating patients with bipolar mood disorders that have not responded to lithium and/or other mood-stabilizers.

2. Uses in Treating Other Disorders

In other embodiments of the invention, the nanoparticulate topiramate compositions are useful in treating or preventing, for example, migraines, neuropathic pain relief, essential type tremor, cluster headache.

"Neuropathic pain" is pain being caused to the peripheral nerve fibers themselves. Descriptions of neuropathic pain by patients typically include words such as burning, shooting, stabbing, or electric like and not aching or crushing. The distribution of pain will be along the course of a particular peripheral nerve or a group of nerves of similar length. For neuropathic pain, nonnarcotic pain relievers are generally not helpful.

"Migraines" and "cluster headaches" are types of headaches. Neurologists diagnose headaches according to the International Headache Society (I.H.S.) Classification System. This system recognizes four primary headache types. The phrase, "primary headache type" means that the headache is not caused by some other disease process. These headache types are migraine, tension, cluster and chronic paroxysmal hemicrania, and miscellaneous. Of these, cluster is by far the most severe headache. The headache intensity is severe enough to make some patients contemplate suicide. These headaches are called cluster because the patient will experience a "cluster" or series of headaches for some period of time and they will then disappear for several months before they recur.

3. Uses in Treating Addictive Behaviors, Including Obesity

In addition to being useful in treating epilepsy and related conditions, new research demonstrates that topiramate is useful in treating a range of conditions potentially associated with addictive behaviors, such as obesity, smoking, alcohol dependence, and drug addiction.

a. Treatment of Obesity

Soon after the epilepsy drug topiramate hit the market in 1996, doctors noticed something unexpected: patients using the anti-seizure medication suddenly began losing weight—rapidly. See R. Stein, "Epilepsy Drugs May Curb Obesity," *Wash. Post*, p. A03 (Oct. 7, 2003). Recent studies designed specifically to test topiramate as a weight-loss aid have found that it helps people, especially those prone to binge eating, to lose—and keep off—significant amounts of weight.

Topiramate has helped obese people lose as much as 10 percent of their body weight. See Bray et al., "A 6-Month Randomized, Placebo-Controlled, Dose-Ranging Trial of Topiramate for Weight Loss in Obesity," *Obesity Research*, 11:722-733 (2003).

One unusual trend observed during the topiramate obesity studies was a consistent decline in weight over the entire study period, enabling people to keep the weight off. No currently approved obesity drug exhibits this property.

Moreover, the proportion of patients who responded to treatment by losing more than 5% of their body weight was high—80% to 88% for one study. The proportion of patients who lost 10% or more of their body weight was also high—59% to 64% for the same study. In addition, researchers observed benefits in low-density lipoprotein (LDL) levels, and high-density lipoprotein (HDL), as well as in the LDL-to-HDL ratio with topiramate.

Obesity has proven to be difficult to target, perhaps because of the complexity of factors governing weight control. Even the most common form of obesity, diet-induced obesity, has a complex pathophysiology for which fundamental protein targets are both poorly understood and involved in multiple metabolic and physiologic pathways such that modifying their activity is fraught with adverse effects. The most notorious obesity treatment was a combination known as fen-phen, which was recalled from the market in 1997 after it was associated with heart valve damage, adverse cardiovascular effects, and other serious ailments in an unacceptably high proportion of recipients. Many other anti-obesity agents have failed in clinical trials. Nothing currently in the clinical trial pipeline to treat obesity appears to be able to overcome these and other limitations.

Moreover, while topiramate has been shown to be useful in treating obesity, there is a concern that the adverse event profile for the drug will make widespread use of topiramate for treating obesity unlikely. The adverse effect profile in mid-to-late stage clinical trials in obesity included memory problems, fatigue, sleepiness, difficulty in concentration, and tingling in the fingers and toes. As a result of this adverse effect profile, Johnson & Johnson decided to discontinue clinical trials for topiramate for treating obesity. See L. Henderson et al., "J&J willl not Pursue Topamax for Obesity," *BTecI News* (Feb. 8, 2002)

Specifically, a Johnson & Johnson sponsored study recently reported that topiramate, used in combination with an intensive behavioural intervention, seems to be safe and effective for weight reduction in newly diagnosed obese, type 2 diabetics who are following a controlled diet. The study comprised 541 randomized patients who were given 60 weeks treatment with topiramate 96 mg/d or 192 mg/d, or placebo, following a six-week placebo run-in period. However, while positive results were observed, the study was terminated prematurely to develop an improved formulation with the potential for enhanced tolerability in this population. Thus, no patient completed the 52-week maintenance phase. During the study, 19% of patients withdrew because of side effects. The most common treatment-related adverse events were related to the central nervous system and included paraesthesia, fatigue, hypoesthesia, injury, and abnormal vision. The most common adverse events resulting in withdrawal were paraesthesia in 5% of patients, depression in 3%, and difficulty with memory in 3%. See J. Stein, "International Diabetes Federation (IDF): Topiramate Shows Potential for Weight Loss Obese Diabetics" (Aug. 26, 2003); (summarizing study results reported on August 25$^{th}$ at the Eighteenth International Diabetes Federation (IDF) Congress, entitled "Safety and Efficacy of topiramate in the treatment of type 2 diabetic obese subjects: a randomised, double blind, placebo controlled trial").

Nanoparticulate topiramate compositions according to the invention can overcome these and other disadvantages with prior art topiramate compositions, because of the improved formulation characteristics as well as enhanced bioavailability of the novel topiramate compositions.

b. Treatment of Alcohol Dependence

In May of 2003, the results of a study designed to determine the effectiveness in treating alcohol dependence were reported at the 2003 Annual Meeting of the American Psychiatric Association. The results showed that patients taking oral topiramate were 6 times more likely to be continuously alcohol-free for at least one month during the three-month trial. Over the same period, those taking the placebo were four times more likely to drink heavily for an entire month during the trial. Not only was self-reported drinking reduced, but a strictly objective lab test measure for evidence of recent alcohol use (plasma GGT) showed the benefit of topiramate. See Johnson et al., "Oral topiramate for treatment of alcohol dependence: a randomized controlled trial," *Lancet*, 361(9370):1666-7 (May 17, 2003).

The study comprised 150 subjects in a 12-week, placebo-controlled, randomized study. All subjects met *Diagnostic and Statistical Manual IV* criteria for alcohol dependence by scoring 8 or higher on the alcohol use disorders identification test. In the 90 days prior to the study, women reported drinking a mean of at least 21 standard drinks per week, and men reported consuming at least 35 standard drinks per week. A "standard drink" is 12 oz of beer, 5 oz of wine, or 1.5 oz of 80-proof liquor. See Johnson et al. Topiramate was given to 75 subjects at 25 mg/day, titrated upwards at 25-50 mg/week to either 300 mg/day or maximum tolerated dose. The remaining 75 patients received escalating placebo tablets. Average daily dose of topiramate at end point was 120 mg/day. See Johnson et al.

The researchers reported that topiramate significantly reduced the amount and severity of drinking. See Johnson et al. Moreover, alcohol-dependent patients frequently have liver disease, one indicator of which is a rise in the plasma level of the enzyme gamma glutamyl transferase (GGT). Notably, topiramate was superior to placebo at significantly reducing the plasma GGT levels during the trial. Further, topiramate was shown to be effective treatment for all types of alcohol-dependent patients.

Topiramate is from a different class of drug than those previously used in the treatment of alcoholism. Thus, topiramate can bring benefits to patients for whom other drugs are not successful.

Nearly 14 million Americans —1 in every 13 adults— abuse alcohol or are alcoholic, according to the National Institutes of Health National Institute on Alcohol Abuse and Alcoholism (NIAAA). Several million more adults engage in risky drinking that could lead to alcohol problems. This behavior includes binge drinking and heavy drinking on a regular basis. In addition, 53% of men and women in the United States report drinking problems in close relatives. Alcohol-related problems cost society about $185 billion per year, the NIAAA estimates.

While topiramate may be useful in treating alcohol dependence, side effects associated with the drug may decrease the utility of the drug. Nanoparticulate topiramate compositions according to the invention can overcome these and other disadvantages with prior art topiramate compositions.

c. Treatment of Nicotine Addiction

In late 2001, the U.S. Department of Energy's Brookhaven National Laboratory reported that topiramate could be a cure for nicotine addiction. See "Therapeutic Drug Blocks Nicotine's Effects on Brain Chemistry" (Nov. 8, 2001);

Nicotine is believed to trigger dependence by reacting with a brain chemical called dopamine, which is associated with pleasure and reward. The Brookhaven National Laboratory ("BNL") study experimented on neurochemical activity in rats. The researchers found that topiramate targets two different neurotransmitter pathways that reduce the excitatory input into the dopamine system, and raise the activity of a brain chemical that inhibits dopamine. Topiramate was also found to increase serotonin, which has been found by previous studies to help reduce the incidence of smoking.

In the study, scientists injected one group of rats with topiramate while another group received control injections of saline. The scientists then gave both groups an acute dose of nicotine and measured dopamine, norepinephrine, and serotonin levels in their brains. Animals given topiramate but no nicotine were also studied to see if topiramate alone had any effect on the neurotransmitters. The scientists also tested the effect of topiramate on dopamine in animals that had been pretreated with nicotine for 14 days prior to the experiment, to serve as a model for humans addicted to the drug.

As expected, animals that received saline and then nicotine showed significant increases in all three brain chemicals. Rats that had been previously "addicted" to nicotine showed even greater elevations in brain dopamine than those that received just the acute dose—similar to what you'd expect to see in a smoker who has a cigarette after a period of not smoking.

Pretreatment with topiramate, however, completely blocked nicotine-triggered increases in norepinephrine and dopamine—and even modulated the dopamine response in the "addicted" animals. Since the brain's dopamine and norepinephrine systems are closely linked, the ability of topiramate to reduce increases in both neurotransmitters suggests that this drug has potential for treating nicotine abuse.

The researchers concluded that the ability of topiramate to increase serotonin activity, while at the same time control dopamine, might make it an effective treatment for nicotine addiction.

While topiramate may be useful in treating nicotine addiction, side effects associated with the drug may decrease the utility of the drug. Nanoparticulate topiramate compositions according to the invention can overcome these and other disadvantages with prior art topiramate compositions.

4. Treatment of Drug Addiction and Addictive Behaviors Generally

The scientific results related to obesity treatment, alcohol dependence, and nicotine addiction have led scientists to explore what could be a new approach for other addictive behaviors. Topiramate appears to help some people control obsessive behaviors, including eating, alcohol abuse, and smoking. It is theorized that topiramate works by tamping down uncontrolled electrical firings of nerve cells that lead to compulsive eating, drinking or smoking in the same way that blocking uncontrolled electrical firing in the brain prevents seizures.

Similar addictions are observed with drugs, such as for example cocaine, heroin, oxycontin, etc. Along with apparently reducing uncontrolled electrical firings in the brain, topiramate seems to affect chemical signals involved in pleasure—serotonin and dopamine.

Thus, topiramate is likely also useful in treating drug addiction, as well as other undesirable addictive behaviors.

While topiramate may be useful in treating drug addiction as well as other addictive behaviors, side effects associated with the drug may decrease the utility of the drug. Nanoparticulate topiramate compositions according to the invention can overcome these and other disadvantages with prior art topiramate compositions.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLE 1

The purpose of this example was to screen several surface stabilizers to determine their suitability for preparing a nanoparticulate dispersion of topiramate.

Aqueous mixtures of 5% (w/w) topiramate and 1.25% (w/w) surface stabilizer, with and without 0.05% docusate sodium (DOSS) (USP), were milled under high energy milling conditions in a NanoMill™ (Elan Drug Delivery, Inc.) (see e.g., WO 00/72973 for "Small-Scale Mill and Method Thereof"), utilizing 500 µm polymeric attrition media (Dow Chemical Co.) for 45 minutes. The surface stabilizers screened were hydroxypropylcellulose (HPC-SL) (USP), Hypromellose (USP), polyvinylpyrrolidone (PVP) C-30 (USP), Plasdone® S630 (ISP) (USP), which is a random copolymer of vinyl acetate and vinyl pyrrolidone, and lysozyme, as shown in the following table.

Following milling, the relative homogeneity of the dispersions was determined based on comparative light microscopy utilizing a Leica oil immersion photo microscopy system (Leica DMRB; Wetzlar,Germany). The results are shown in Table 1.

TABLE 1

Results of Surface Stabilizer Screening

| Composition | Homogeneity of Resulting Dispersion |
| --- | --- |
| 5% (w/w) topiramate 1.25% (w/w) HPC-SL | Very Good |
| 5% (w/w) topiramate 1.25% (w/w) HPC-SL 0.05% DOSS | Good |
| 5% (w/w) topiramate 1.25% (w/w) Hypromellose | Excellent |
| 5% (w/w) topiramate 1.25% (w/w) Hypromellose 0.05% DOSS | Excellent |
| 5% (w/w) topiramate 1.25% (w/w) PVP | Poor |
| 5% (w/w) topiramate 1.25% (w/w) PVP 0.05% DOSS | Very good |
| 5% (w/w) topiramate 1.25% (w/w) Plasdone ® S630 | Very good |
| 5% (w/w) topiramate 1.25% (w/w) Plasdone ® S630 0.05% DOSS | Very good |
| 5% (w/w) topiramate 1.25% (w/w) lysozyme | Good |

It was concluded that hypromellose was the lead candidate for scale-up, based on the results of a comparative light microscopy test.

EXAMPLE 2

The purpose of this example was to prepare a nanoparticulate dispersion of topiramate.

An aqueous mixture of 15% (w/w) topiramate, 3% (w/w) Hypromellose USP, and 0.05% DOSS USP was milled under high energy milling conditions in a DYNO®-Mill KDL (Willy A. Bachofen AG, Maschinenfabrik, Basel, Switzerland) equipped with a 150 cc batch chamber and utilizing 500 µm polymeric attrition media (Dow Chemical Co.) for 4 hours. Particle size analysis was performed with a Horiba LA-910 particle size analyzer (Irvine, Calif.). The mean particle size of the milled topiramate dispersion was 110 nm.

Following particle size reduction, the mean particle size (nm) of the topiramate dispersion was measured at 5° C., 25° C., and at 40° C. at various time intervals, as shown below in Table 2.

TABLE 2

Mean Particle Size (nm) Following Milling of a Topiramate Dispersion

| Time | 5° C. | 25° C. | 40° C. |
| --- | --- | --- | --- |
| 4 hours | 110 | | |
| 1 day | 158 | 154 | 166 |
| 5 days | 172 | 167 | 157 |

TABLE 2-continued

Mean Particle Size (nm) Following Milling of a Topiramate Dispersion

| Time | 5° C. | 25° C. | 40° C. |
|---|---|---|---|
| 8 days | 190 | 171 | 201 |
| 29 days | 175 | 145 | 235 |
| 54 days | 529 | | |

The results demonstrate the stability of the nanoparticulate dispersion of topiramate over an extended time period.

EXAMPLE 3

The purpose of this example was to determine the in vivo pharmacokinetics of nanoparticulate topiramate compositions.

Dog Study Protocol

Eight male Beagle dogs were not fasted and had food available prior to dosing. Each dog received the following two formulations:

Formulation # 1: Liquid Dispersion of Nanoparticulate Topiramate 12 g of topiramate (Elan Pharmaceuticals, Inc.) was added to a solution containing 2.4 g hypromellose USP (HPMC) (Shinetzu), 40 mg docusate sodium USP (DOSS) (Cytec), and 80 g water q.s. WFI (Water for Injection, Abbott Laboratories).

This mixture was then milled for 160 min. in a DYNO-Mill KDL (Willy A. Bachofen A G, Maschinenfabrik, Basel, Switzerland) with PolyMill™-500 polymeric media (Dow Chemical Co.).

The final mean (volume average) particle size of the nanoparticulate topiramate dispersion was 183 nm, as measured on a Horiba LA-910 particle size analyzer (Horiba Instruments, Irvine, Calif.). Sufficient diluent (DI water) was supplied and added to a 150 mg/g concentrate of the nanoparticulate topiramate dispersion to achieve a final concentration of 50 mg/g.

Formulation # 2: Tablet of Conventional Microparticulate Topiramate

TOPAMAX® Tablets (Ortho-McNeil Pharmaceutical, Inc.), 25 mg.

In Phase I, four dogs received a single oral gavage dose of 25 mg of the nanoparticulate topiramate composition (Topiramate Formulation #1) (0.5 g of a 50 mg/g), followed by an approximately 10 mL tap water flush of the gavage tube. In addition, four different dogs were given a 25 mg Topamax® tablet dose (Topiramate Formulation #2).

In Phase 2, after a one week washout period, the four dogs which received the oral gavage dose of Topiramate Formulation #1 in Phase 1 received a 25 mg Topamax® tablet dose (Topiramate Formulation #2). The four dogs which received the Topamax® tablet dose (Topiramate Formulation #2) in Phase 1 received a single oral gavage dose of the nanoparticulate topiramate composition (Topiramate Formulation #1), followed by an approximately 10 mL tap water flush of the gavage dose.

Blood samples (approximately 1 mL) were drawn at specified time points into pre-cooled tubes containing sodium heparin. The samples were placed on wet ice/ice block following collection. Plasma was separated and stored frozen at approximately −70° C. The protocols of Phase I and II are summarized in Table 3, below.

TABLE 3

| Phase | Compound | #males | Dose route | # articles | Dose (mg) | Matrix collected |
|---|---|---|---|---|---|---|
| 1 | Nanoparticulate Topiramate Dispersion | 4 | PO | NA | 25 | Blood[a] |
| 2 | Topamax ® | 4 | Tablet | 1 | 25 | Blood[a] |

The summary of the results of the pharmacokinetic tests are shown below in Table 4 and in FIGS. 1 and 2, and the raw data is shown in Table 5. FIG. 1 graphically shows the average concentration (ng/mL) of Formulation #1 and #2 over a 25 hour time period, and FIG. 2 graphically shows the average concentration (ng/mL) of Formulation #1 and #2 over a 1 hour time period.

TABLE 4

| | $C_{max}$ (ng/mL) | $T_{max}$ (hours) | AUC (ng hr/ml) |
|---|---|---|---|
| Formulation 1 | 1688.78 | 0.687 | 12008.273 |
| Topamax ® | 1878.2 | 1.531 | 13592.199 |

TABLE 5

| Treatment | Dog | Cmax (ng/mL) | Tmax (hours) | AUClast (ng hr/ml) | AUCINF (observed) (ng hr/ml) |
|---|---|---|---|---|---|
| Nanoparticulate Topiramate Dispersion | A | 1732.98 | 0.50 | 12830.37 | 13406.21 |
| | B | 1495.43 | 0.33 | 9122.03 | 9546.03 |
| | C | 2008.57 | 0.25 | 13538.65 | 14082.49 |
| | D | 1963.74 | 0.75 | 14008.02 | 14637.54 |
| | E | 1785.52 | 0.75 | 11624.62 | 12085.61 |
| | F | 768.81 | 2.00 | 7864.06 | 8563.12 |
| | G | 1646.89 | 0.75 | 13148.19 | 13678.43 |
| | H | 2108.30 | 0.17 | 13930.25 | 14459.54 |

| Treatment | Dog | Cmax | Tmax | AUClast | AUCINF (observed) |
|---|---|---|---|---|---|
| TOPAMAX ® Tablet | A | 1912.81 | 1.00 | 14349.04 | 14906.04 |
| | B | 1797.61 | 1.00 | 14521.30 | 15183.95 |
| | C | 2130.23 | 0.50 | 13967.65 | 14505.60 |
| | D | 2410.57 | 1.00 | 12266.89 | 12714.00 |
| | E | 2007.58 | 1.50 | 15053.38 | 15819.91 |
| | F | 821.26 | 6.00 | 10403.61 | 11405.12 |
| | G | 2018.93 | 0.50 | 12268.48 | 12619.10 |
| | H | 1926.61 | 0.75 | 15907.25 | 16566.29 |

$T_{max}$ for the nanoparticulate topiramate composition was less than half that of the conventional microcrystalline topiramate composition. Therefore, the nanoparticulate topiramate composition exhibited an onset of activity which is about twice that of the conventional non-nanoparticulate topiramate composition.

While the $C_{max}$ and AUC were slightly less than that observed for the conventional microcrystalline topiramate composition, it is possible that nanoparticulate topiramate compositions having, for example, different concentrations of active agent and/or surface stabilizer, different surface stabilizers, or formulated into a different dosage form, would exhibit preferably $C_{max}$ and/or AUC profiles as compared to a conventional non-nanoparticulate topiramate composition.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A nanoparticulate topiramate composition comprising:
   (a) particles of topiramate or a salt thereof, wherein the topiramate particles have an effective average particle size of less than 2 microns; and
   (b) at least one surface stabilizer.

2. The composition of claim 1, wherein the effective average particle size of the nanoparticulate topiramate particles is selected from the group consisting of less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 150 nm, less than 140 nm, less than 130 nm, less than 120 nm, less than 110 nm, less than 100 nm, less than 90 nm, less than 80 nm, less than 70 nm, less than 60 nm, and less than 50 nm.

3. The composition of claim 2, wherein at least about 70%, at least about 90%, at least about 95%, or at least about 99% of the topiramate particles have a particle size less than the effective average particle size.

4. The composition of claim 1, wherein the topiramate is selected from the group consisting of a crystalline phase, an amorphous phase, and a semi-crystalline phase.

5. The composition of claim 1, wherein the composition is formulated for administration selected from the group consisting of oral, pulmonary, rectal, opthalmic, colonic, parenteral, intracistemal, intravaginal, intraperitoneal, local, buccal, nasal, and topical administration.

6. The composition of claim 1, wherein the composition further comprises one or more pharmaceutically acceptable excipients, carriers, or a combination thereof.

7. The composition of claim 1, wherein the topiramate is present in an amount selected from the group consisting of from about 99.5% to about 0.001%, from about 95% to about 0.1%, and from about 90% to about 0.5%, by weight, based on the total combined dry weight of the topiramate and at least one surface stabilizer, not including other excipients.

8. The composition of claim 1, wherein the at least one surface stabilizer is present in an amount selected from the group consisting of from about 0.5% to about 99.999%, from about 5.0% to about 99.9%, and from about 10% to about 99.5%, by weight, based on the total combined dry weight of the topiramate and at least one surface stabilizer, not including other excipients.

9. The composition of claim 1, comprising at least two surface stabilizers.

10. The composition of claim 1, wherein the surface stabilizer is selected from the group consisting of an anionic surface stabilizer, a cationic surface stabilizer, a zwitterionic surface stabilizer, and an ionic surface stabilizer.

11. The composition of claim 10, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oils, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-derivatized phospholipid, PEG-derivatized cholesterols, PEG-derivatized vitamin A, PEG-derivatized vitamin E, and random copolymers of vinyl acetate and vinyl pyrrolidone.

12. The composition of claim 10, wherein the at least one cationic surface stabilizer is selected from the group consisting of a polymer, a biopolymer, a polysaccharide, a cellulosic, an alginate, a nonpolymeric compound, a phospholipid, zwitterionic stabilizers, poly-n-methylpyridinium, anthryul pyridinium chloride, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt), Poly(2-methacryloxyethyl trimethylammonium bromide), poloxamines, lysozyme, alginic acid, carrageenan, POLYOX, cationic lipids, sulfonium, phosphonium, quarternary ammonium compounds, stearyltrimethylammonium chloride, benzyl-di (2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium bromide, $C_{12-15}$dimethyl hydroxyethyl ammonium chloride, $C_{12-15}$dimethyl hydroxyethyl ammonium bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecyldimethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts, amines, protonated quaternary acrylamides, methylated quaternary polymers, and cationic guar.

13. The composition of claim 12, wherein the amine is selected from the group consisting of alkylamines, dialkylamines, alkanolamines, polyethylenepolyamines, N,N-dialkylaminoalkyl acrylates, vinyl pyridine, amine salts, lauryl amine acetate, stearyl amine acetate, alkylpyridinium salt, alkylimidazolium salt, amine oxides, and, imide azolinium salts.

14. The composition of claim 10, wherein the cationic surface stabilizer is a nonpolymeric compound selected from the group consisting of benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

15. The composition according to any of claims 10, 12, 13, or 14, wherein the composition is bioadhesive.

16. The composition of claim 1, comprising hypromellose, docusate sodium, or a combination thereof as surface stabilizers.

17. The composition of claim 1, further comprising a topiramate composition having an effective average particle size of greater than 2 microns.

18. The composition of claim 1, further comprising at least one additional nanoparticulate topiramate composition having an effective average particle size of less than 2 microns, wherein said additional nanoparticulate topiramate composition has an effective average particle size which is different than the effective average particle size of the nanoparticulate topiramate composition of claim 1.

19. The composition of claim 1, additionally comprising at least one non-topiramate active agent.

20. The composition of claim 19, wherein said active agent is selected from the group consisting of amino acids, proteins, peptides, nucleotides, anti-obesity drugs, nutraceuticals, dietary supplements, central nervous symptom stimulants, carotenoids, corticosteroids, elastase inhibitors, anti-fungals, alkylxanthine, oncology therapies, anti-emetics, analgesics, opioids, antipyretics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobactenal agents, antineoplastic agents, immunosuppressants, antithyroid agents, antiviral agents, anxiolytics, sedatives, astringents, alpha-adrenergic receptor blocking agents, beta-adrenoceptor blocking agents, blood products, blood substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin and biphosphonates, prostaglandins, radio-pharmaceuticals, sex hormones, anti-allergic agents, stimulants, anoretics, sympathomimetics, thyroid agents, vasodilators, vasomodulator, xanthines, Mu receptor antagonists, Kappa receptor antagonists, non-narcotic analgesics, monoamine uptake inhibitors, adenosine regulating agents, cannabinoids, Substance P antagonists, neurokinin-1 receptor antagonists, and sodium channel blockers.

21. The composition of claim 20, wherein said nutraceutical is selected from the group consisting of lutein, folic acid, fatty acids, fruit extracts, vegetable extracts, vitamin supplements, mineral supplements, phosphatidylserine, lipoic acid, melatonin, glucosamine/chondroitin, Aloe Vera, Guggul, glutamine, amino acids, green tea, lycopene, whole foods, food additives, herbs, phytonutrients, antioxidants, flavonoid constituents of fruits, evening primrose oil, flax seeds, fish oils, marine animal oils, and probiotics.

22. The composition of any of claims 19, 20, or 21, wherein at least one non-topiramate active agent has an effective average particle size of less than 2 microns.

23. The composition of any of one of claims 19, 20, or 21, wherein at least one non-topiramate active agent has an effective average particle size of greater than 2 microns.

24. The composition of claim 1 formulated into a liquid dosage form, wherein the dosage form has a viscosity of less than 2000 mPa·s at a shear rate of 0.1 (1/s).

25. The composition of claim 24 having a viscosity at a shear rate of 0.1 (1/s) selected from the group consisting of from about 2000 mPa·s to about 1 mPa·s, from about 1900 mPa·s to about 1 mPa·s, from about 1800 mPa·s to about 1 mP·s, from about 1700 mPa·s to about 1 mPa·s, from about 1600 mPa·s to about 1 mP·s, from about 1500 mPa·s to about 1 mPa·s, from about 1400 mPa·s to about 1 mP·s, from about 1300 mP·s to about 1 mPa·s, from about 1200 mP·s to about 1 mPa·s, from about 1100 mPa·s to about 1 mPa·s, from about 1000 mPa·s to about 1 mPa·s, from about 900 mPa·s to about 1 mPa·s, from about 800 mPa·s to about 1 mPa·s, from about 700 mPa·s to about 1 mPa·s, from about 600 mPa·s to about 1 mP·s, from about 500 mPa·s to about 1 mPa·s, from about 400 mPa·s to about 1 mPa·s, from about 300 mPa·s to about 1 mPa·s, from about 200 mPa·s to about 1 mPa·s, from about 175 mPa·s to about 1 mP·s, from about 150 mPa·s to about 1 mP·s, from about 125 mPa·s to about 1 mPa·s, from about 100 mPa·s to about 1 mPa·s, from about 75 mP·s to about 1 mPa·s, from about 50 mPa·s to about 1 mPa·s, from about 25 mPa·s to about 1 mPa·s, from about 15 mPa·s to about 1 mPa·s, from about 10 mP·s to about 1 mPa·s, and from about 5 mPa·s to about 1 mPa·s.

26. The composition of claim 1 formulated into a liquid dosage form, wherein the viscosity of the dosage form is selected from the group consisting of less than 1/200, less than 1/100, less than 1/50, less than 1/25, and less than 1/10 of the viscosity of a liquid dosage form of a conventional non-nanoparticulate topiramate composition, at the same concentration per ml of topiramate.

27. The composition of claim 1 formulated into a liquid dosage form, wherein the viscosity of the dosage form is selected from the group consisting of less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, and less than 90% of the viscosity of a liquid dosage form of a conventional non-nanoparticulate topiramate composition at the same concentration per ml of topiramate.

28. The composition of claim 1 formulated into a liquid dosage form, wherein the amount of topiramate per ml is equal to or greater than the amount of topiramate per ml of a liquid dosage form of a conventional non-nanoparticulate topiramate composition.

29. The composition of claim 1, wherein upon administration the composition redisperses such that the topiramate particles have an effective average particle size selected from the group consisting of less than 2 microns, less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 150 nm, less than 100 nm, less than 75 nm, and less than 50 nm.

30. The composition of claim 1, wherein the composition redisperses in a biorelevant media such that the topiramate particles have an effective average particle size selected from the group consisting of less than 2 microns, less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 150 nm, less than 100 nm, less than 75 nm, and less than 50 nm.

31. The composition of claim 1, wherein the composition does not produce significantly different absorption levels when administered under fed as compared to fasted conditions.

32. The composition of claim 1, wherein upon administration the $T_{max}$ is less than that of a conventional non-nanoparticulate topiramate composition, administered at the same dosage.

33. The composition of claim 32, wherein in comparative pharmacokinetic testing with a conventional non-nanoparticulate topiramate composition, administered at the same dosage, the nanoparticulate composition exhibits a $T_{max}$ selected from the group consisting of less than 100%, less than 90%, less than 80%, less than 70%, less than 60%, less than 50%, less than 40%, less than 30%, less than 25%, less than 20%, less than 15%, and less than 10% of the $T_{max}$ exhibited by the non-nanoparticulate topiramate composition.

34. The composition of claim 1, wherein following administration the composition has a $T_{max}$ selected from the group consisting of less than 2 hours, less than 110 min., less than 100 min., less than 90 min., less than 80 min. less than 70 min., less than 60 min., less than 50 mm., less than 40 min., less than 30 min., less than 25 min., less than 20 min., less than 15 min., less than 10 min., less than 5 min., and less than 3 min.

35. The composition of claim 1, wherein upon administration the $C_{max}$ of the composition is greater than the $C_{max}$ of a conventional non-nanoparticulate topiramate composition, administered at the same dosage.

36. The composition of claim 35, wherein in comparative pharmacokinetic testing with a conventional non-nanoparticulate topiramate composition, administered at the same dosage, the nanoparticulate composition exhibits a $C_{max}$ selected from the group consisting of greater than 5%, greater than 10%, greater than 15%, greater than 20%, greater than 30%, greater than 40%, greater than 50%, greater than 60%, greater than 70%, greater than 80%, greater than 90%, greater than 100%, greater than 110%, greater than 120%, greater than 130%, greater than 140%, and greater than 150% than the $C_{max}$ exhibited by the non-nanoparticulate topiramate composition.

37. The composition of claim 1, wherein the therapeutically effective amount of topiramate is selected from the group consisting of 1/6, 1/5, 1/3$^{rd}$, and 1/2 of the therapeutically effective amount of a conventional non-nanoparticulate topiramate composition.

38. The nanoparticulate topiramate composition of claim 1 formulated into a dosage form for oral administration, wherein the relative bioavailability of the nanoparticulate topiramate composition compared to a solution is selected from the group consisting of greater than 80%, greater than 85%, greater than 90%, and greater than 95%.

39. A method of making a nanoparticulate topiramate composition comprising contacting topiramate particles with at least one surface stabilizer for a time and under conditions sufficient to provide a nanoparticulate topiramate composition having an effective average particle size of less than 2 microns.

40. The method of claim 39, wherein said contacting comprises grinding.

41. The method of claim 40, wherein said grinding comprises wet grinding.

42. The method of claim 39, wherein said contacting comprises homogenizing.

43. The method of claim 39, wherein said contacting comprises:
  (a) dissolving the topiramate particles in a solvent;
  (b) adding the resulting topiramate solution to a solution comprising at least one surface stabilizer; and
  (c) precipitating the solubilized topiramate and at least one surface by the addition thereto of a non-solvent.

44. The method of claim 39, wherein the effective average particle size of the nanoparticulate topiramate particles is selected from the group consisting of less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 150 nm, less than 140 nm, less than 130 nm, less than 120 nm, less than 110 nm, less than 100 nm, less than 90 nm, less than 80 nm, less than 70 nm, less than 60 nm, and less than 50 nm.

45. The method of claim 44, wherein at least 70%, at least 90%, at least 95%, or at least 99% of the topiramate particles have a particle size less than the effective average particle size.

46. The method of claim 3, wherein the topiramate is selected from the group consisting of a crystalline phase, an amorphous phase, and a semi-crystalline phase.

47. The method of claim 39, wherein the composition is formulated for administration selected from the group consisting of oral, pulmonary, rectal, opthalmic, colonic, parenteral, intracisternal, intravaginal, intraperitoneal, local, buccal, nasal, and topical administration.

48. The method of claim 39, wherein the composition further comprises one or more pharmaceutically acceptable excipients, carriers, or a combination thereof.

49. The method of claim 39, wherein the topiramate is present in an amount selected from the group consisting of from about 99.5% to about 0.001%, from about 95% to about 0.1%, and from about 90% to about 0.5%, by weight, based on the total combined dry weight of the topiramate and at least one surface stabilizer, not including other excipients.

50. The method of claim 39, wherein the at least one surface stabilizer is present in an amount selected from the group consisting of from about 0.5% to about 99.999%, from about 5.0% to about 99.9%, and from about 10% to about 99.5%, by weight, based on the total combined dry weight of the topiramate and at least one surface stabilizer, not including other excipients.

51. The method of claim 39, comprising at least two surface stabilizers.

52. The method of claim 39, wherein the surface stabilizer is selected from the group consisting of an anionic surface stabilizer, a cationic surface stabilizer, a zwitterionic surface stabilizer, and an ionic surface stabilizer.

53. The method of claim 52, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oils, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-derivatized phospholipid, PEG-derivatized cholesterols, PEG-derivatized vitamin A, PEG-derivatized vitamin E, and random copolymers of vinyl acetate and vinyl pyrrolidone.

54. The method of claim 52, wherein the at least one cationic surface stabilizer is selected from the group consisting of a polymer, a biopolymer, a polysaccharide, a cellulosic, an alginate, a nonpolymeric compound, a phospholipid, zwitterionic stabilizers, poly-n-methylpyridinium, anthryul pyridinium chloride, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt), Poly(2-methacryloxyethyl trimethylammonium bromide), poloxamines, lysozyme, alginic acid, carrageenan, POLYOX, cationic lipids, sulfonium, phosphonium, quarternary ammonium compounds, stearyltrimethylammonium chloride, benzyl-di (2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium bromide, $C_{12-15}$dimethyl hydroxyethyl ammonium chloride, $C_{12-15}$dimethyl hydroxyethyl ammonium bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl $(C_{12-18})$dimethylbenzyl ammonium chloride, N-alkyl $(C_{14-18})$dimethyl-benzyl ammonium chloride, N-tetradecylidmethylbenzyl ammonium chloride monohydrate, dimethyl didecyl ammonium chloride, N-alkyl and $(C_{12-14})$ dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts, amines, protonated quaternary acrylamides, methylated quaternary polymers, and cationic guar.

55. The method of claim 54, wherein the amine is selected from the group consisting of alkylamines, dialkylamines, alkanolamines, polyethylenepolyamines, N,N-dialkylaminoalkyl acrylates, vinyl pyridine, amine salts, lauryl amine acetate, stearyl amine acetate, alkylpyridinium salt, alkylimidazolium salt, amine oxides, and, imide azolinium salts.

56. The method of claim 52, wherein the cationic surface stabilizer is a nonpolymeric compound selected from the group consisting of benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectorite, stearyl trihydroxyethyl propylenediamine dihydrofluoride, tallowtrimonium chloride, and hexadecyltrimethyl ammonium bromide.

57. The method according to any of claims 52, 54, 55 or 56, wherein the composition is bioadhesive.

58. The method of claim 39, comprising hypromellose, docusate sodium, or a combination thereof as surface stabilizers.

59. The method of claim 39, wherein after preparation of the nanoparticulate topiramate composition, a second topiramate composition having an effective average particle size of greater than 2 microns is combined with the nanoparticulate topiramate composition.

60. The method of claim 39, wherein either prior or subsequent to preparation of the nanoparticulate topiramate composition, at least one non-topiramate active agent is added to the nanoparticulate topiramate composition.

61. The method of claim 60, wherein said non-topiramate active agent is selected from the group consisting of amino acids proteins, peptides, nucleotides, anti-obesity drugs, nutraceuticals, dietary supplements, carotenoids, central nervous system stimulants, corticosteroids, elastase inhibitors, anti-fungals, alkylxanthine, oncology therapies, anti-emetics, analgesics, opioids, antipyretics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, alpha-adrenergic receptor blocking agents, beta-adrenoceptor blocking agents, blood products, blood substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin and biphosphonates, prostaglandins, radio-pharmaceuticals, sex hormones, antiallergic agents, stimulants, anoretics, sympathomimetics, thyroid agents, vasodilators, vasomodulator, xanthines, Mu receptor antagonists, Kappa receptor antagonists, non-narcotic analgesics, monoamine uptake inhibitors, adenosine regulating agents, cannabinoids, Substance P antagonists, neurokinin-1 receptor antagonists, and sodium channel blockers.

62. The method of claim 61, wherein said nutraceutical is selected from the group consisting of lutein, folic acid, fatty acids, fruit extracts, vegetable extracts, vitamin supplements, mineral supplements, phosphatidylserine, lipoic acid, melatonin, glucosamine/chondroitin, Aloe Vera, Guggul, glutamine, amino acids, green tea, lycopene, whole foods, food additives, herbs, phytonutrients, antioxidants, flavonoid constituents of fruits, evening primrose oil, flax seeds, fish oils, marine animal oils, and probiotics.

63. The method of any of claims 60, 61, or 62, wherein at least one non-topiramate active agent has an effective average particle size of less than 2 microns.

64. The method of any of claims 60, 61, or 62, wherein at least one non-topiramate active agent has an effective average particle size of greater than 2 microns.

65. A method of treating a subject in need with a nanoparticulate topiramate formulation comprising administering to the subject an effective amount of a nanoparticulate composition comprising topiramate particles and at least one surface stabilizer, wherein the topiramate particles have an effective average particle size of less than 2 microns.

66. The method of claim 65, wherein the subject has a condition selected from the group consisting of seizures, mood disorders, post traumatic stress syndrome (PTSD), Bipolar Disorder, mania, depression, personality disorders, bipolar mood instability, schizophrenia, psychosis, bipolar spectrum disorders, and rapid-cycling bipolar disorders.

67. The method of claim 65, wherein the subject has a mood disorder or a bipolar mood disorder which has not been adequately controlled by other medications.

68. The method of claim 65, wherein the subject is being treated for obesity.

69. The method of claim 65, wherein the subject is being treated for alcohol dependence.

70. The method of claim 65, wherein the subject is being treated for nicotine addiction.

71. The method of claim 65, wherein the subject is being treated for drug addiction.

72. The method of claim 65, wherein the subject is being treated for an undesirable addictive behavior.

73. The method of claim 65, wherein the subject is being treated for migraines.

74. The method of claim 65, wherein the subject is being treated for neuropathic pain relief.

75. The method of claim 65, wherein the subject is being treated for essential type tremor.

76. The method of claim 65, wherein the subject is being treated for cluster headaches.

77. The method of claim 65, wherein said subject is a human.

78. The method of claim 65, wherein the effective average particle size of the nanoparticulate topiramate particles is selected from the group consisting of less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 150 nm, less than 140 nm, less than 130 nm, less than 120 nm, less than 110 nm, less than 100 nm, less than 90 nm, less than 80 nm, less than 70 nm, less than 60 nm, and less than 50 nm.

79. The method of claim 65, wherein at least 70%, at least 90%, at least 95%, or at least 99% of the topiramate particles have a particle size less than the effective average particle size.

80. The method of claim 65, wherein the topiramate is selected from the group consisting of a crystalline phase, an amorphous phase, and a semi-crystalline phase.

81. The method of claim 65, wherein the composition is formulated for administration selected from the group consisting of oral, pulmonary, rectal, opthalmic, colonic, parenteral, intracisternal, intravaginal, intraperitoneal, local, buccal, nasal, and topical administration.

82. The method of claim 65, wherein the composition further comprises one or more pharmaceutically acceptable excipients, carriers, or a combination thereof.

83. The method of claim 65, wherein the topiramate is present in an amount selected from the group consisting of from about 99.5% to about 0.001%, from about 95% to about 0.1%, and from about 90% to about 0.5%, by weight, based on the total combined dry weight of the topiramate and at least one surface stabilizer, not including other excipients.

84. The method of claim 65, wherein the at least one surface stabilizer is present in an amount selected from the group consisting of from about 0.5% to about 99.999%, from about 5.0% to about 99.9%, and from about 10% to about 99.5%, by weight, based on the total combined dry weight of the topiramate and at least one surface stabilizer, not including other excipients.

85. The method of claim 65, comprising at least two surface stabilizers.

86. The method of claim 65, wherein the surface stabilizer is selected from the group consisting of an anionic surface stabilizer, a cationic surface stabilizer, a zwitterionic surface stabilizer, and an ionic surface stabilizer.

87. The method of claim 86, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oils, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; lysozyme, PEG-derivatized phospholipid, PEG-derivatized cholesterols, PEG-derivatized vitamin A, PEG-derivatized vitamin E, and random copolymers of vinyl acetate and vinyl pyrrolidone.

88. The method of claim 86, wherein the at least one cationic surface stabilizer is selected from the group consisting of a polymer, a biopolymer, a polysaccharide, a cellulosic, an alginate, a nonpolymeric compound, a phospholipid, zwitterionic stabilizers, poly-n-methylpyridinium, anthryul pyridinium chloride, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt), Poly(2-methacryloxyethyl trimethylammonium bromide), poloxamines, lysozyme, alginic acid, carrageenan, POLYOX, cationic lipids, sulfonium, phosphonium, quaternary ammonium compounds, stearyltrimethylammonium chloride, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium bromide, $C_{12-15}$dimethyl hydroxyethyl ammonium chloride, $C_{12-15}$dimethyl hydroxyethyl ammonium bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl $(C_{12-18})$dimethylbenzyl ammonium chloride, N-alkyl $(C_{14-18})$dimethyl-benzyl ammonium chloride, N-tetradecylidmethylbenzyl ammonium chloride monohydrate, dimethyl didecyl ammonium chloride, N-alkyl and $(C_{12-14})$ dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt, alkyl pyridinium salts, amines, protonated quaternary acrylamides, methylated quaternary polymers, and cationic guar.

89. The method of claim 88, wherein the amine is selected from the group consisting of alkylamines, dialkylamines, alkanolamines, polyethylenepolyamines, N,N-dialkylaminoalkyl acrylates, vinyl pyridine, amine salts, lauryl amine acetate, stearyl amine acetate, alkylpyridinium salt, alkylimidazolium salt, amine oxides, and, imide azolinium salts.

90. The method of claim 86, wherein the cationic surface stabilizer is a nonpolymeric compound selected from the group consisting of benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectonte, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

91. The method according to any of claims 86, 88, 89, or 90, wherein the composition is bioadhesive.

92. The method of claim 6, comprising hypromellose, docusate sodium, or a combination thereof as surface stabilizers.

93. A pharmaceutical composition of an anticonvulsant agent comprising solid particles of the agent coated with one or more surface modifiers, wherein the particles have an average effective particle size of less than 50 nm to less than 2000 nm.

94. The composition of claim 93, wherein the surface modifier is selected from the group consisting of: anionic surfactants, cationic surfactants, zwitterionic surfactants, nonionic surfactants, surface active biological modifiers, and combinations thereof.

95. The composition of claim 94, wherein the anionic surfactant is selected from the group consisting of: alkyl sulfonates, alkyl phosphates, triethanolamine stearate, sodium lauryl sulfate, sodium dodecylsulfate, alkyl polyoxyethylene sulfates, sodium alginate, dioctyl sodium sulfosuccinate, sodium carboxymethylcellulose, and calcium carboxymethylcellulose.

96. The composition of claim 94, wherein the cationic surfactant is selected from the group consisting of quaternary ammonium compounds, benzalkonium chloride, cetyltrimethylammonium bromide, lauryldimethylbenzylammonium chloride, dimethyldioctadecylammomium bromide, dioleyoltrimethylammonium propane, dimyristoyltrimethylammonium propane, dimethylaminoethanecarbamoyl cholesterol, 1,2-dialkylglycero-3-alkylphosphocholine and n-octylamine.

97. The composition of claim 94, wherein the cationic surfactant is a phospholipid, and wherein the phospholipid is natural or synthetic.

98. The composition of claim 93, wherein the surface modifier is a pegylated phospholipid.

99. The composition of claim 94, wherein the nonionic surfactant is selected from the group consisting of: polyoxyethylene fatty alcohol ethers, polyoxyethylene sorbitan fatty acid esters, polyoxyethylene fatty acid esters, sorbitan esters, glycerol monostearate, polyethylene glycols, polypropylene glycols, cetyl alcohol, cetostearyl alcohol, polyoxyethylene-polyoxypropylene copolymers, polaxamines, methylcellulose, hydroxy propylcellulose, hydroxy propylmethylcellulose, noncrystalline cellulose, polysaccharides, starches, hydroxyethylstarch, polyvinyl alcohol, and polyvinylpyrrolidone.

100. The composition of claim 94, wherein the surface active biological modifier is selected from the group consisting of proteins, polysaccharides, and combinations thereof.

101. The composition of claim 100, wherein the polysaccharide is selected from the group consisting of starches and chitosans.

102. The composition of claim 100, wherein the protein is casein.

103. The composition of claim 93, wherein the surface modifier comprises a copolymer of oxyethylene and oxypropylene.

104. The composition of claim 103, wherein the copolymer of oxyethylene and oxypropylene is a block copolymer.

105. The composition of claim 93, further comprising a pH adjusting agent.

106. The composition of claim 105, wherein the pH adjusting agent is selected from the group consisting of hydrochloric acid, phosphoric acid, acetic acid, succinic acid, citric acid, sodium hydroxide, glycine, arginine, and lysine.

107. The composition of claim 106, wherein the pH adjusting agent is added to the composition to bring the pH of the composition within the range of from about 3 to about 11.

* * * * *